United States Patent [19]

Schurman et al.

[11] Patent Number: 4,506,626

[45] Date of Patent: Mar. 26, 1985

[54] APPARATUS FOR CONTROLLING THE PROPORTIONS OF A FLUID

[76] Inventors: Richard H. Schurman; John W. Schurman, both of Bothell; Richard W. Clark, Seattle; Steven Reiter, Lynnwood, all of Wash.

[21] Appl. No.: 423,119

[22] Filed: Sep. 24, 1982

Related U.S. Application Data

[62] Division of Ser. No. 317,539, Nov. 2, 1981.

[51] Int. Cl.³ .................. B05B 12/08; B05B 12/14
[52] U.S. Cl. .................... 118/665; 118/688; 118/691; 427/8
[58] Field of Search .............. 8/400; 356/410, 411; 118/665, 688, 691; 427/8

[56] References Cited

U.S. PATENT DOCUMENTS

| | | | |
|---|---|---|---|
| 3,062,963 | 11/1962 | Douty | 356/411 X |
| 4,189,335 | 2/1980 | Evans et al. | 427/10 |
| 4,338,351 | 7/1982 | Bloom et al. | 427/8 |

Primary Examiner—Shrive P. Beck

[57] ABSTRACT

This invention is directed to the use of two or more light waves having separate and distinct wave lengths. The light waves are directed to a fluid. The initial detected relative intensities of the light waves is known. After the light waves have left the fluid the final relative intensities can be determined. By knowing the relative shift in the initial intensities to the final intensities it is possible to determine a characteristic of the fluid. With this characteristic of the fluid it is possible to take appropriate action to change the characteristic of the fluid or it may be desirable to take no action with respect to the characteristic of the fluid.

25 Claims, 24 Drawing Figures

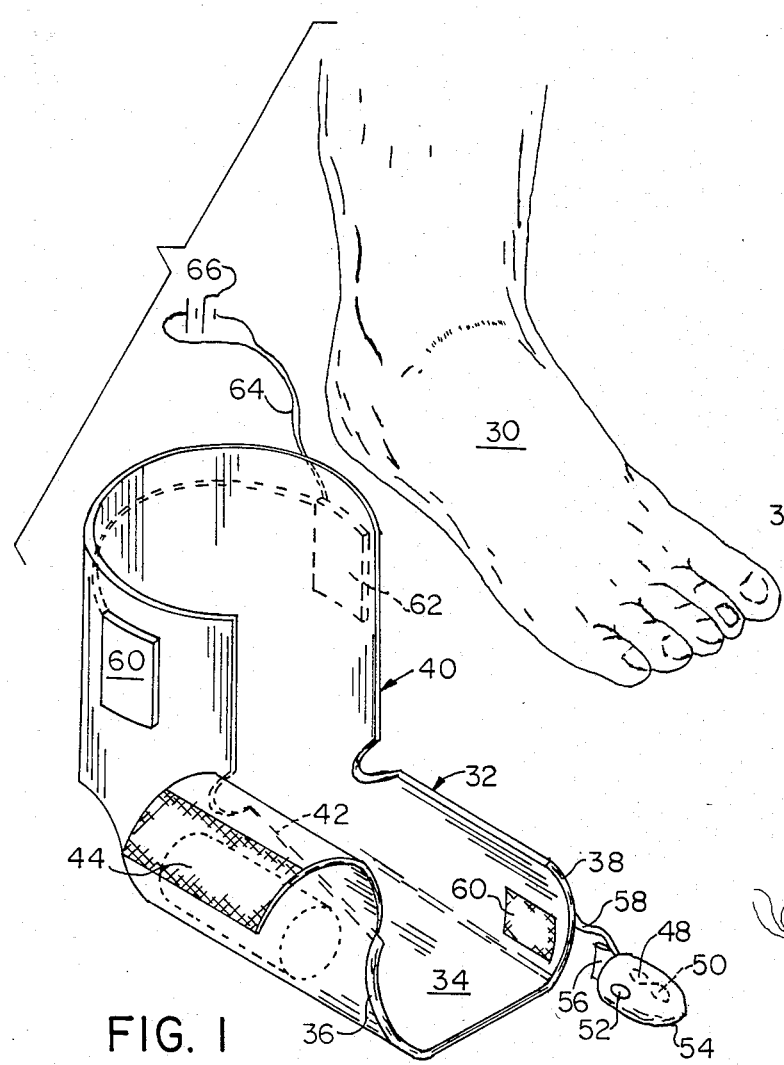
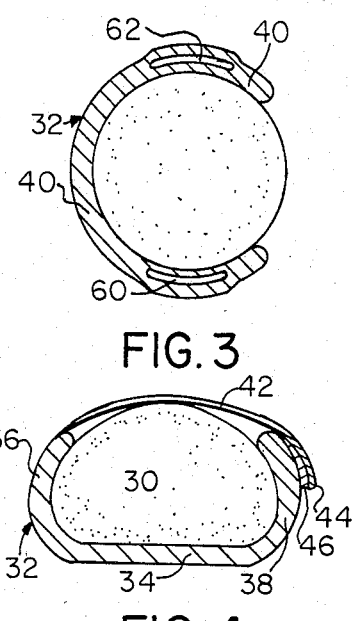
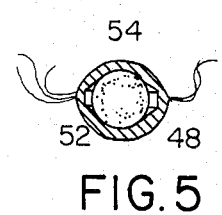
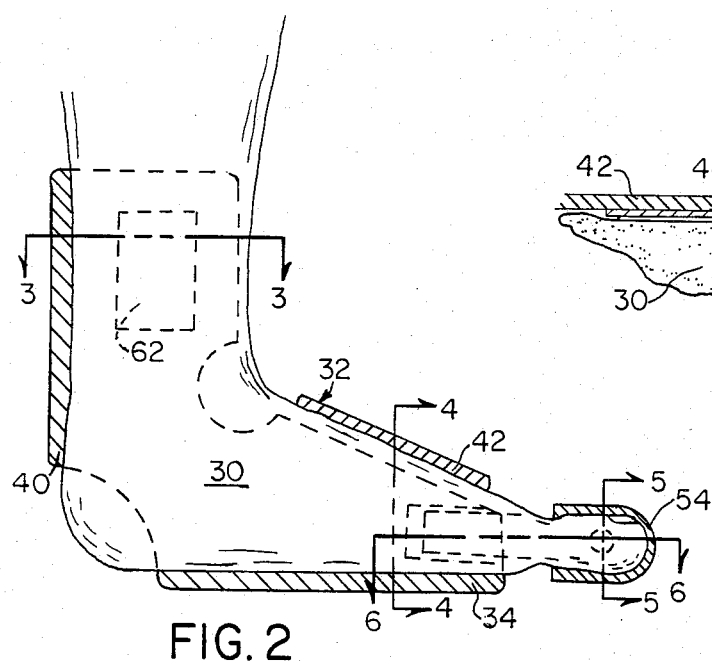
FIG. 1
FIG. 2
FIG. 3
FIG. 4
FIG. 5
FIG. 6

APPARATUS FOR CONTROLLING THE PROPORTIONS OF A FLUID

This patent application is a divisional patent application of co-pending patent application Ser. No. 06/317,539, filing data of Nov. 2, 1981 entitled APNEA MONITOR.

Also, there are three other co-pending divisional patent applications of the above-identified patent application and these are Ser. Nos. 06/423,117; 06/423,178; and, 06/423,118, all filed on Sept. 24, 1982 and all entitled APNEA MONITOR.

THE BACKGROUND OF THE INVENTION

This invention has its basis in a discussion of developing a solid state device that utilizes a non-filtered light source of monitor in a transcutaneous manner the physiological status of gas in the blood of a human being. The purpose is to develop a more reliable method and apparatus to determine the onset of apnea and cyanosis in a non-invasive manner.

The definitions of apnea, cyanosis and transcutaneous as stated in Webster's 7th New Collegiate Dictionary, copyright 1965 by G & C Merriam Company are as follows:

Apnea or Apnoea, (n)—transient cessation of respiration; (adj.)—Apneic

Cyanosis, (n)—dark blue color, a bluish or purplish discoloration (as of skin) due to deficient oxygenation of the blood; (adj.)—Cyanotic Transcutaneous, (adj.)—entering through the skin (infection) (innoculation).

We investigated commercially available apnea monitors. Our investigation showed that there was no apnea monitor which used non-filtered light from two sources of different wave lengths to indicate the onset of apnea and cyanosis. A number of articles have been written on "Sudden Infant Syndrome" which has been given the acronym SIDS or "Crib Death". It is estimated that 10,000 babies in the United States die every year from SIDS.

A number of articles have been written on SIDS and also apnea monitors. In the August-September 1980 issue, Volume 5, No. 10 and 11, of HEALTH DEVICES, published monthly by the Emergency Care Research Institute, 5200 Butler Pike, Plymouth Meeting, PA 19462 and in the "WESTERN HEAITH NEWS", September 1081, published monthly by Syndicate Magazines, Inc. 6 E. 43rd Street, New York, NY 10017, are two interesting articles. Again, there have been numerous articles published on SIDS.

In the "HEALTH DEVICES" article it was stated: "Most apnea monitors in the market today operate via impedance pnumography. A small current in the 20–120 kHz frequency range is passed across the thoracic cavity. The small impedance changes due to air entering and leaving the lungs, and "blood welling" from pressure changes in the thoracic cavity are carried by this current as a voltage change. This change is, in turn, interpreted by the monitor as a breath."

If the baby does not breathe for a period of time lasting longer than about twenty seconds there may occur, if the episodes are left unchecked, a life threatening progression of hypoxia, brain damage and death.

If the baby dies the effect upon the parents and the relatives may be severe. For example, the parents and relatives may go into a deep depression or have a complete mental breakdown or a lifelong guilt feeling haunted by the thought that the baby's death may be somehow their fault. Another side effect is that the death of the baby may lead to divorce between the parents and the breakup of the family.

After the investigation we found that we could use light emitting diodes as a source of the desired wave length as contrasted with impedance pneumography.

We investigated the color change in blood, viz., hemoglobin, with the increase in carbon dioxide in the blood. The color of the hemoglobin changes from a red where there is oxyhemoglobin to a blue where there is carboxyhemoglobin. With the change in the color of the blood from red to blue there is an indication of an increase in the concentration of carbon dioxide in the blood. With an infant, a child less than one year old, there is little calcium in the bones and the light will pass through the tissue and also the solid matter of the bone to be. This is so with respect to the toe of an infant less than one year of age. A light will pass through the tissue and also the material which will become bone upon the maturing of the infant. In this manner it is possible to detect and to monitor the change in color of the blood and use this as an indication of the buildup or increase in concentration of carbon dioxide in the bloodstream.

Apnea is the episodic or cylical episode in the cessation of breathing. In an infant this is more critical than in an adult as an infant breathes more rapidly than an adult, or it may be stated, that the frequency of breathing with an infant is greater than the frequency of breathing with an adult. A result of this is that with an infant it is more critical to have an adequate exchange of oxygen or carbon dioxide in the bloodstream. With an adult the frequency of breathing is in the range of eight to twelve times per minute. With an infant less than one year of age the frequency of breathing is in the range of twenty to thirty times per minute. As a result an infant less than one year of age who has apnea for just a few seconds misses the vital transfer of oxygen for carbon dioxide in the bloodstream.

In the normal brain the medulla is a control center for sending of electrical impulses to the respiratory system for expansion and contraction of the lungs to take in fresh air with a high concentration of oxygen and to exhale gas with a higher concentration or carbon dioxide than the fresh air. The medulla receives its signal based on the amount of carbon dioxide in the blood. In a baby that has missed breathing for five or six seconds there is a buildup in the concentration of carbon dioxide in the bloodstream. Another way of stating this is that the baby may have missed two cycles of breathing. As a result there is an increase in the concentration of carbon dioxide in the bloodstream and a threat to the life of the baby. If this increase in the concentration of carbon dioxide in the bloodstream occurs in a chronic situation then the medulla becomes conditioned so as to ignore some of the signals to it to the effect that there is an unusually large increase in the concentration of carbon dioxide in the bloodstream. With the medulla so conditioned then the medulla may not, promptly, send signals to respiratory system to inhale fresh air having a low concentration of carbon dioxide. In other words, the increase in the concentration of carbon dioxide in the blood acts as a carbon dioxide drive mechanism in the brain. The result is that the medulla does not send the appropriate signals to the respiratory system. A terminal result of this increase in the carbon dioxide in the blood is the death of an infant. It is possible to try to resuscitate the infant but because of the high concentration of carbon dioxde in the blood the brain does not respond to the resuscitation efforts and the infant or victim cannot be revived.

With this belief and knowledge we consider that it is necessary to have a detection system for detecting the increase in the concentration of carbon dioxide in the blood and also an accompaning warning system. The detection system and the warning system must detect the increase in the carbon dioxide in the blood within the time period of five or six seconds and emit a warning. If the increase in carbon dioxide in the blood is not detected in about five or six seconds the result may be a fatality.

With this information and belief we consider that if it be possible to detect the increase in the concentration of carbon dioxide in the blood then a stimulus may be applied to the infant and the infant will inhale and take fresh air into the lungs. The stimulus can be of a non-invasive auditory nature and not an electrical nature.

Prior to this invention, and to the best of our information and knowledge, the apnea monitors and sensing units relied upon impedance pneumography. Further, there was a time delay of approximately ten to thirty seconds so that in that time period there was a large increase in the concentration of carbon dioxide in the blood of the infant. This large increase in the concentration of carbon dioxide in the blood of the infant made it difficult, if not impossible, to resuscitate the infant.

The commercially available apnea monitors give a quantitative indication of the frequency of respiration of the infant. Our apnea monitor gives a qualitative indication of the change of the concentration of carbon dioxide in the blood. Our apnea monitor will function within the first five to six seconds of the increase in the concentration of the carbon dioxide in the blood.

Our above comments with respect to the infant are also applicable to an adult suffering from apnea. The frequency of breathing of an adult is less than the frequency of the breathing of an infant but at certain times with an adult there may be apnea and our invention can be used to overcome the apnea of an adult. An example of this is an individual who snores heavily. If the individual stops snoring heavily he may be having an apnea episode. One way of relieving this individual of the apnea episode is to shake the individual or agitate the individual or stick an elbow in the ribs of the individual to start the individual breathing again. This condition is referred to as "sleep apnea".

THE GENERAL DESCRIPTION OF THE INVENTION

This invention utilizes two or more sources of light. The sources of light have different wave lengths. The light is transmitted through part of the body of the infant. One desirable part of the body of the infant is the toe. There is a sensing means for sensing the wave length of the light or different lights after passing through the toe. These sensing means can give an indication of the qualitative change in the blood of the infant such as an increase in the concentration of carbon dioxide in the blood of the infant. If the qualitative change of the carbon dioxide in the infant increases to too high a concentration of carbon dioxide then an audible alarm can be activated. A suitable audible alarm is a bell or the like. The infant is startled and gasps for air. In gasping for air the infant inhales air which has a low concentration of carbon dioxide and a high concentration of oxygen and exhales a gas which has a high concentration of carbon dioxide. In this manner the infant is stimulated to inhale air having a low concentration of carbon dioxide and a high concentration of oxygen and the condition of apnea is relieved.

THE DRAWINGS

FIG. 1 is an exploded view of the combination of a bootie and a foot which embodies the apparatus in accordance with the invention;

FIG. 2 is a verticle longitudinal cross-section view of the bootie and the foot of an infant and a toe-cap on the toe of the infant;

Figure 7:
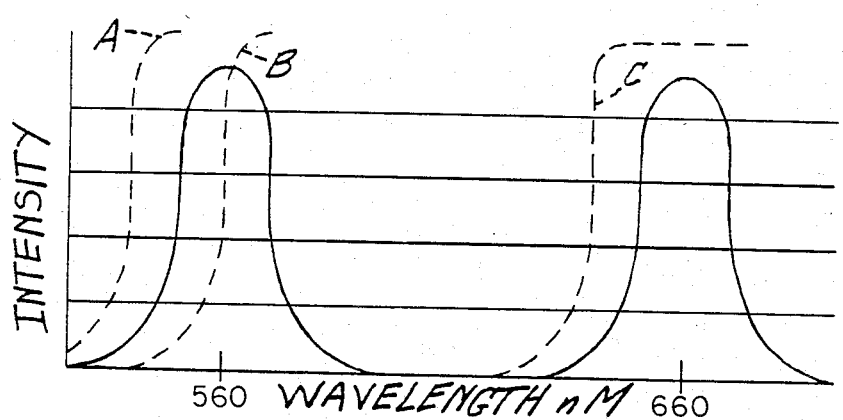
Figure 8:
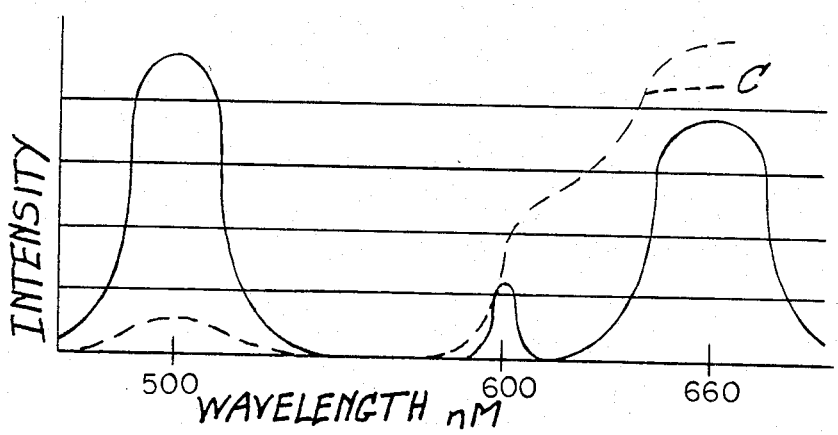
Figure 9:
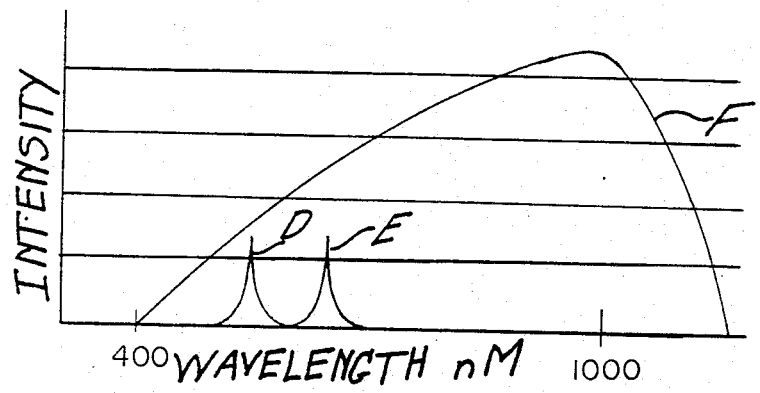
Figure 10:
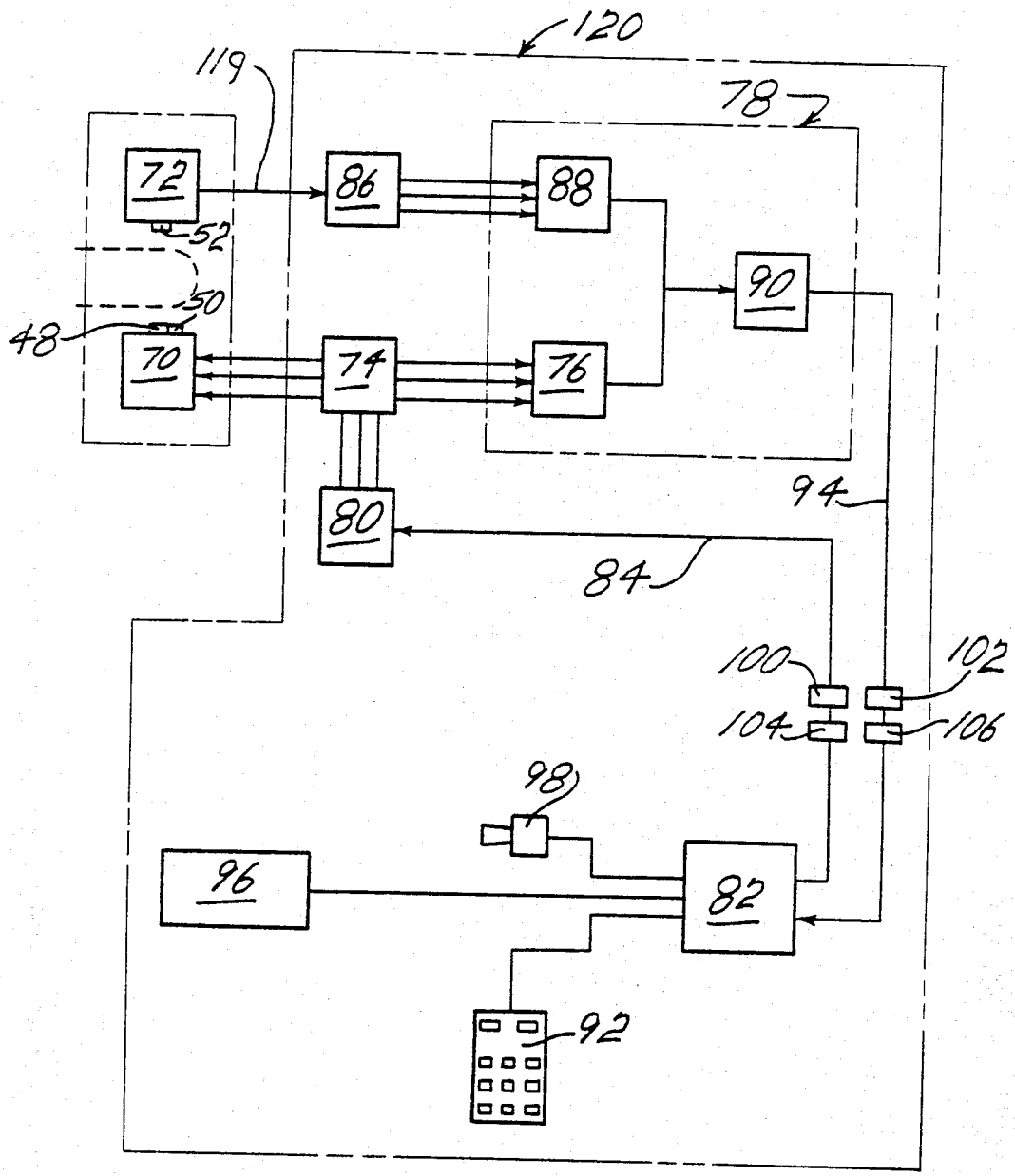
Figure 14:
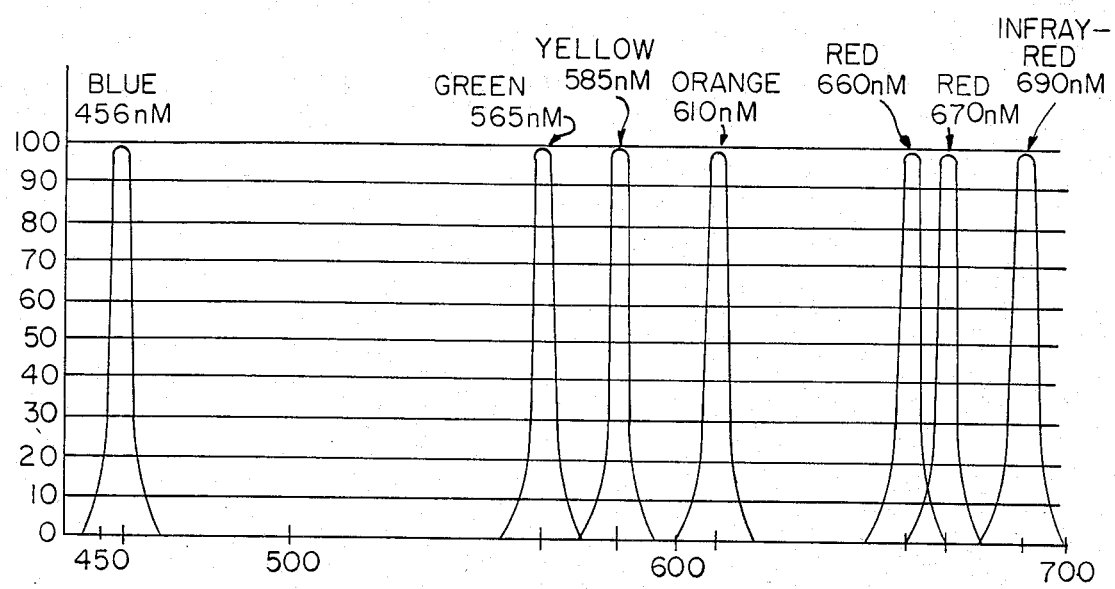
Figure 12:
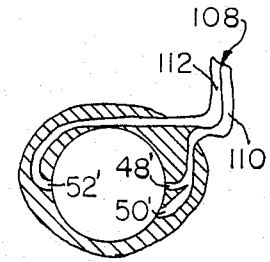
Figure 11:
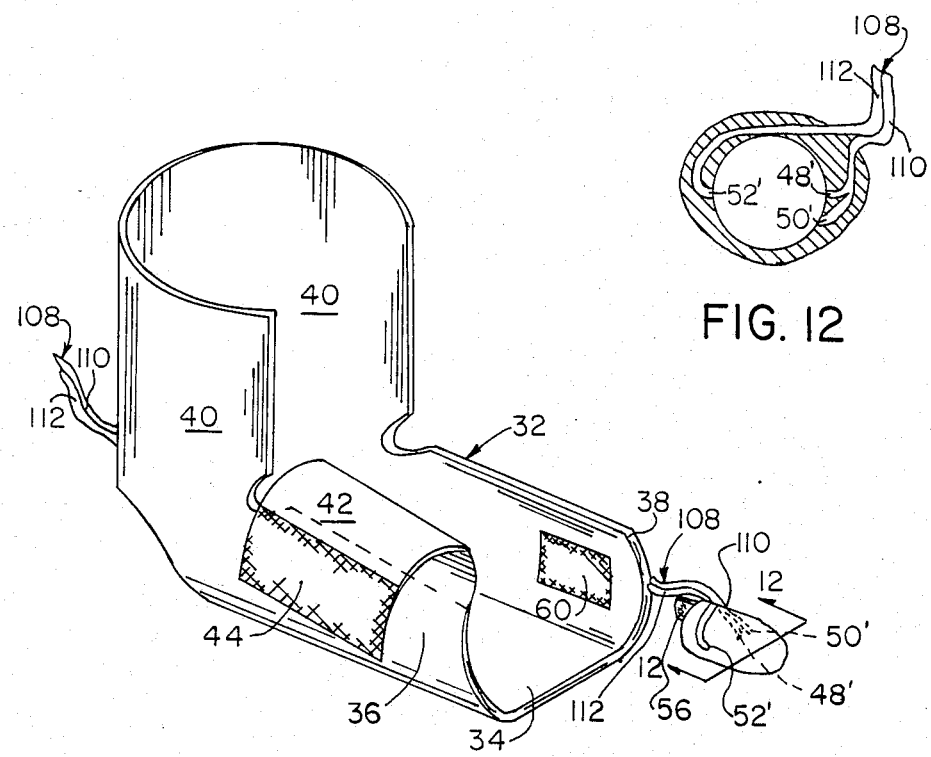
Figure 13:
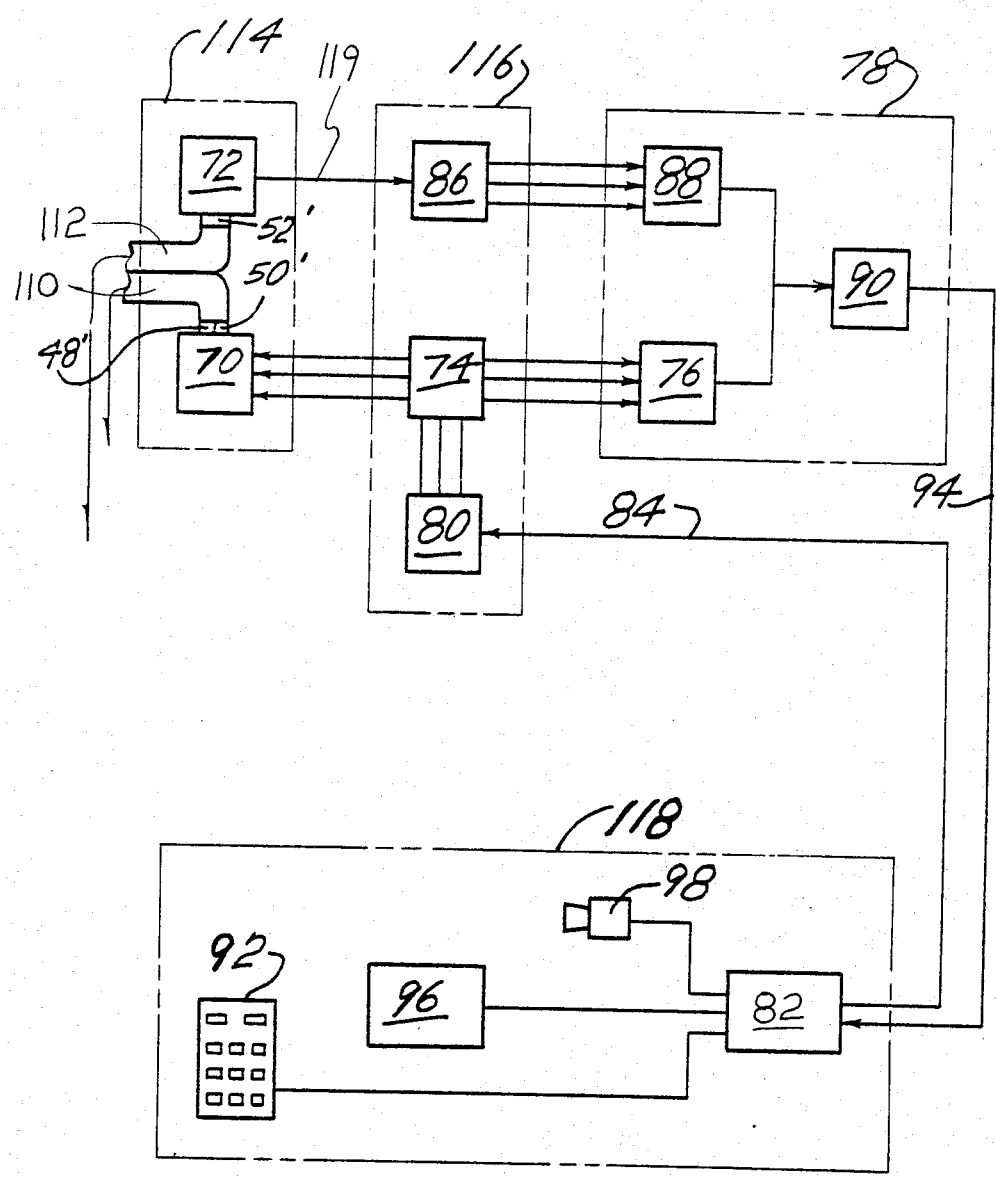
Figure 15:
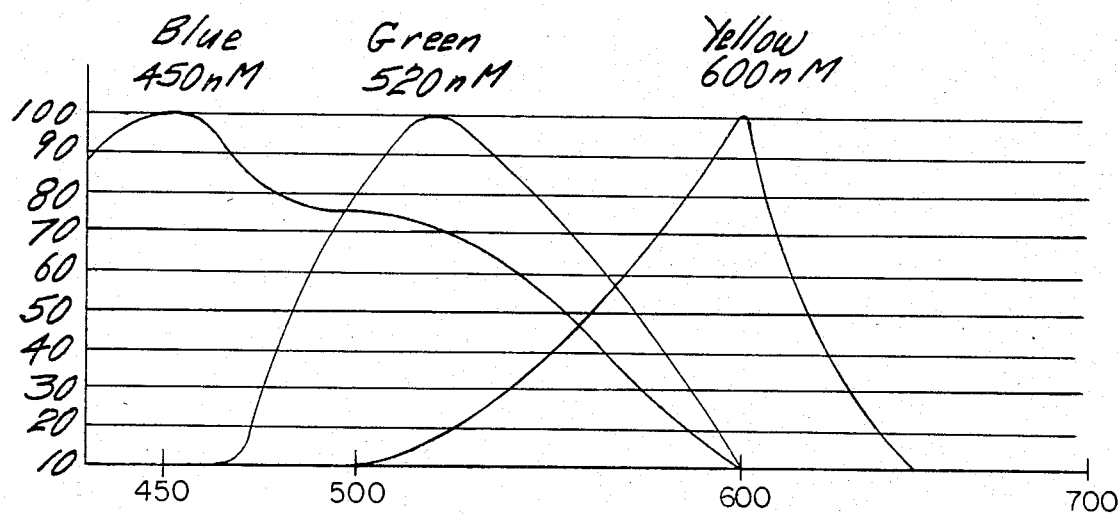
Figure 16:
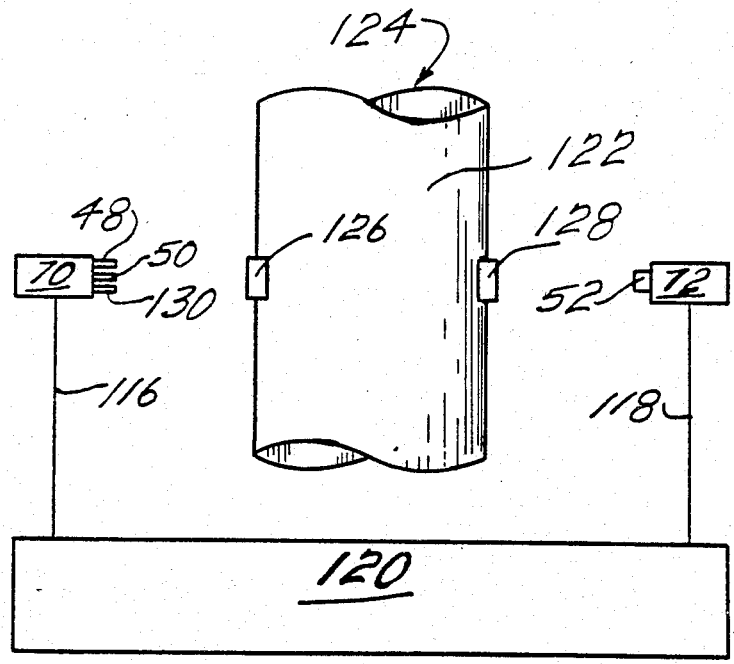
Figure 17:
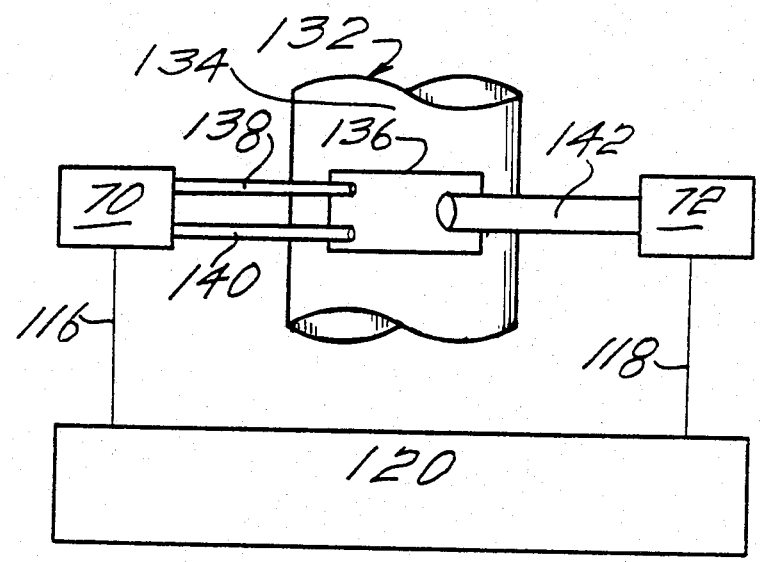
Figure 18:
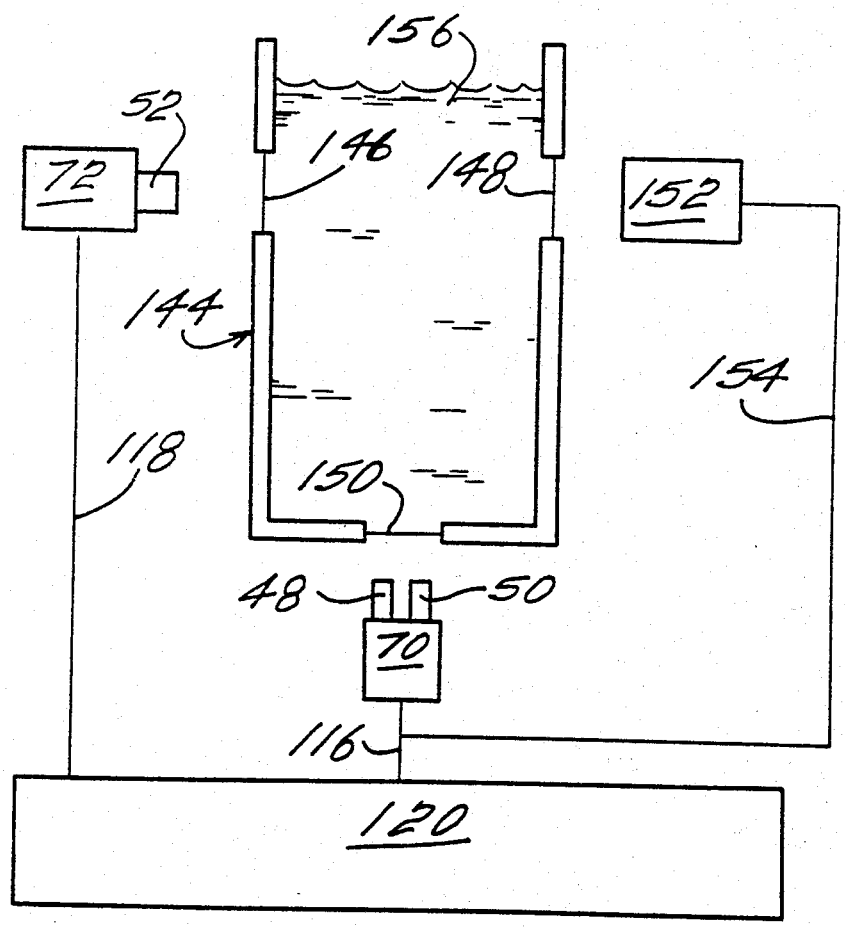
Figure 19:
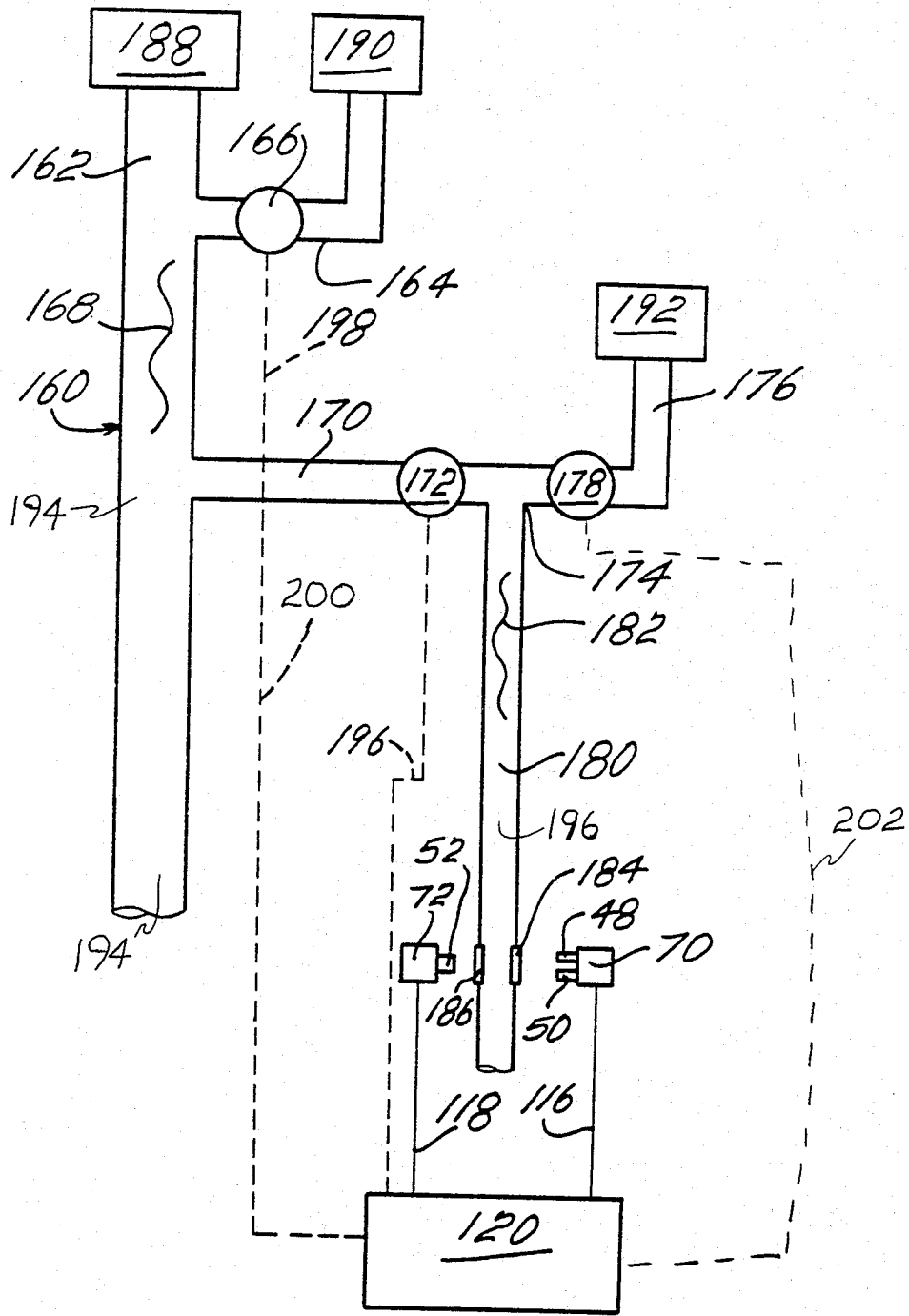
Figure 20:
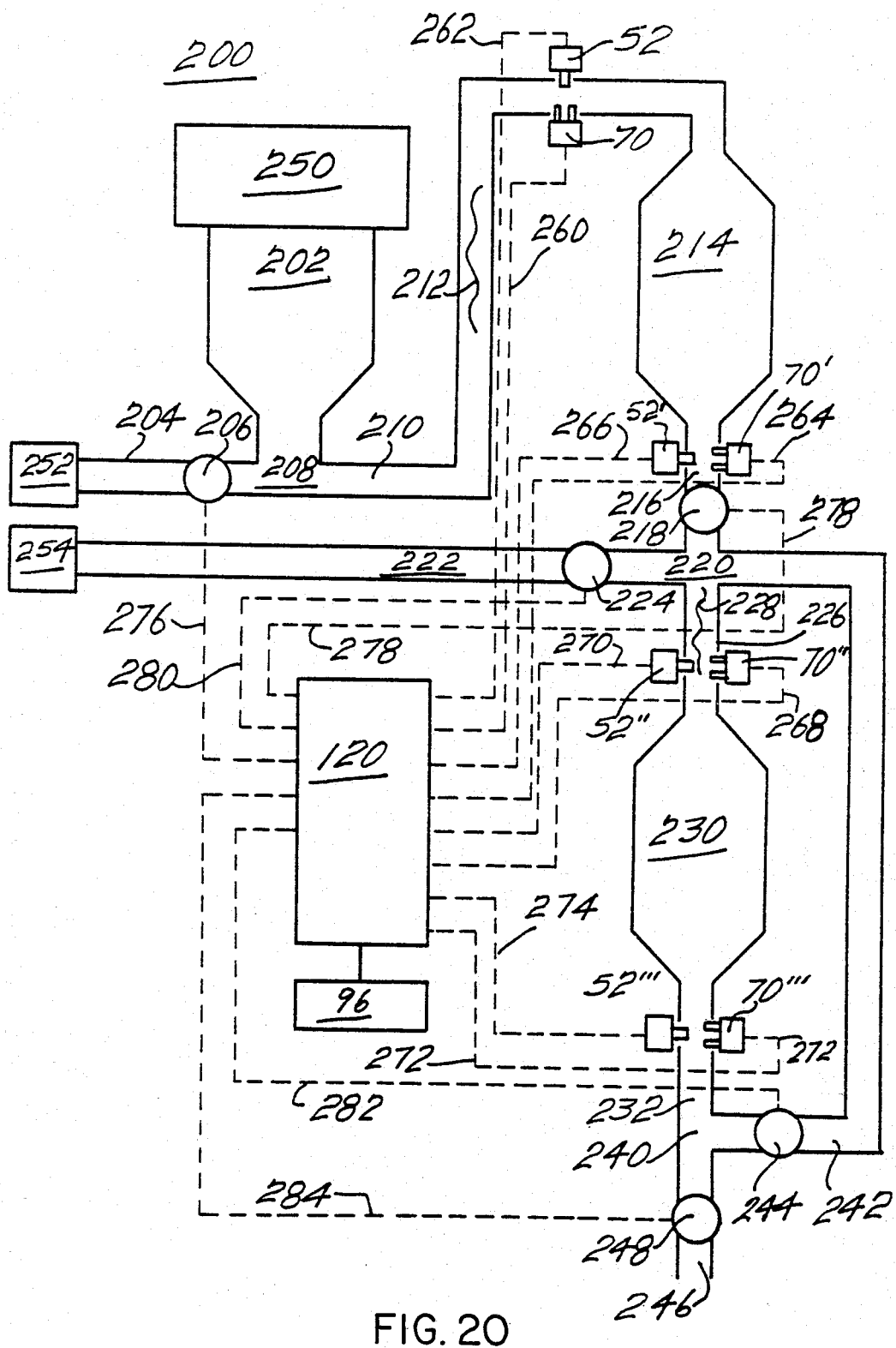
Figure 21:
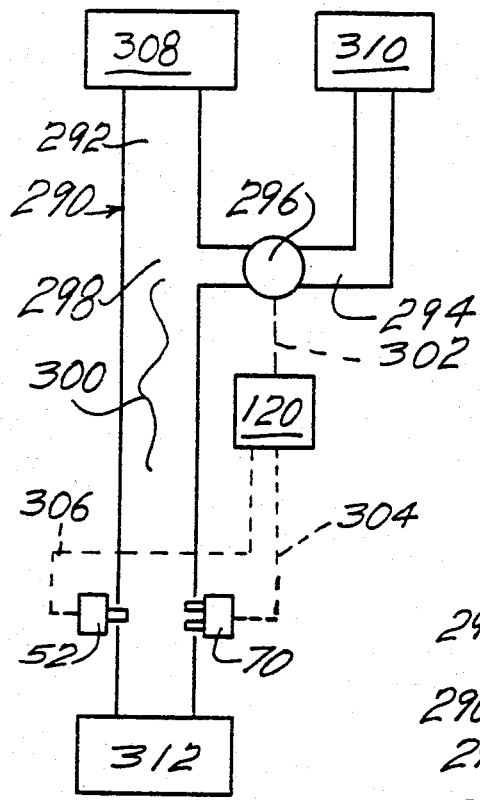
Figure 22:
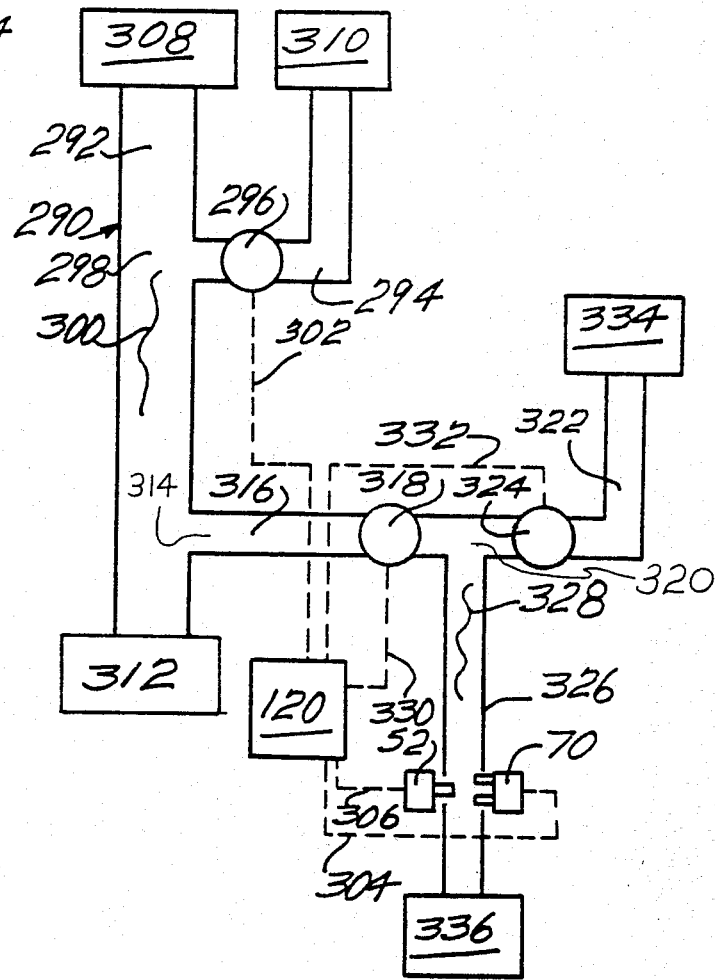
Figure 23:
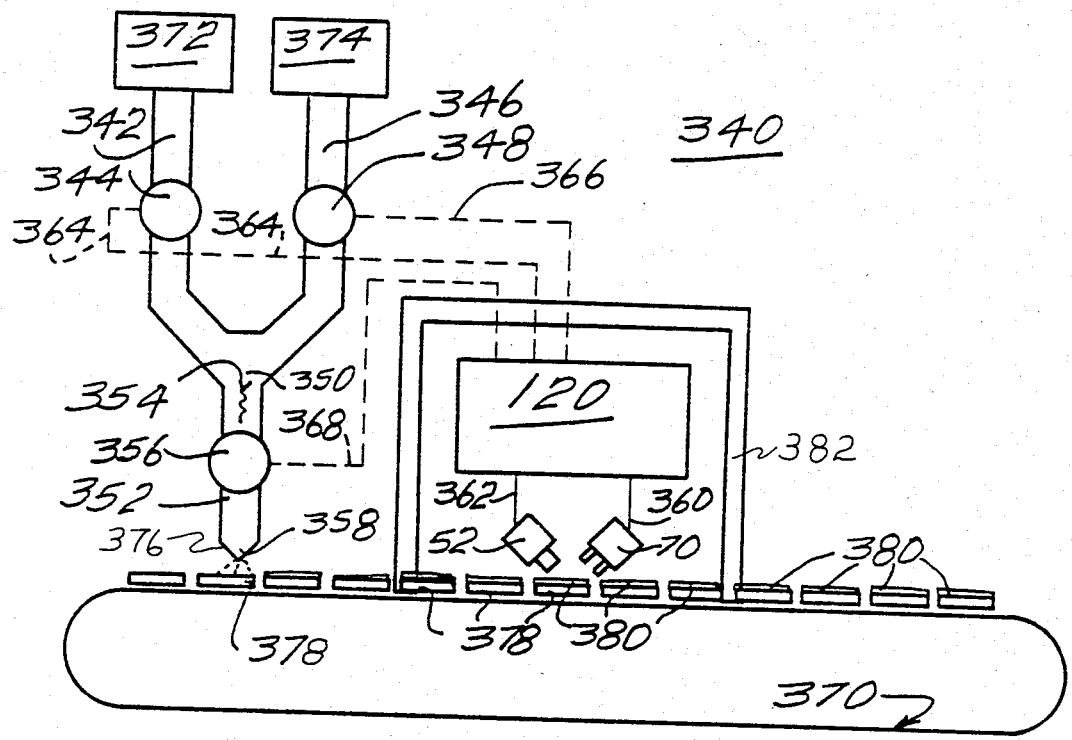
Figure 24:
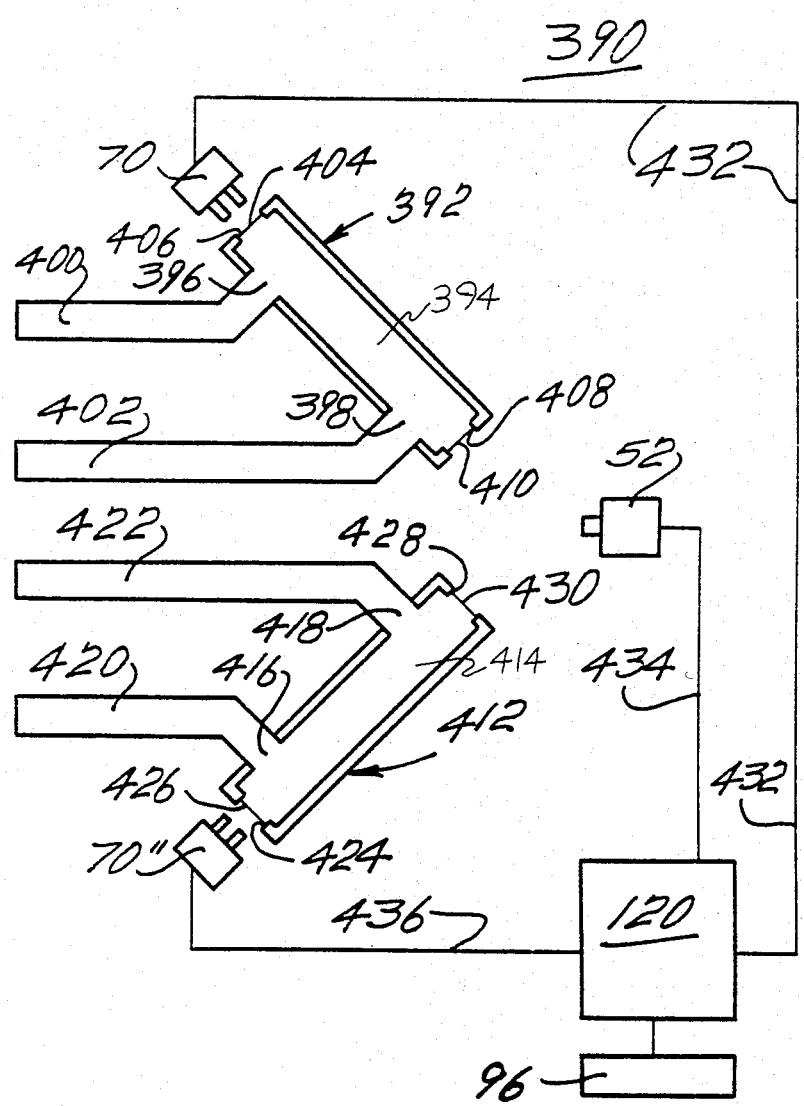

FIG. 3, taken on line 3—3 of FIG. 2, is a lateral cross-sectional view illustrating the bootie in the ankle area of the infant;

FIG. 4, taken on line 4—4 of FIG. 2, is a lateral cross-sectional view of the bootie on the foot of the infant in an area between the arch of the foot and the balls of the foot;

FIG. 5, taken on line 5—5 of FIG. 2, is a lateral cross-sectional view of the light sources and receiver of light as applied to the toe of the foot of the infant;

FIG. 6, is a fragmentary longitudinal view taken on line 6—6 of FIG. 2 and illustrates the bootie and the sources of light and the pickup for the light from the sources after having passed through the toe of the infant;

FIG. 7, is a graph illustrating a plot of the intensity of the light versus the wave length of the light for two lights from two sources of light having different wave lengths;

FIG. 8, is a graph illustrating a plot of the intensity versus the wave length from two sources of light and a medium through which the light will be transmitted;

FIG. 9, is a plot of the intensity versus the wave length of light and is the responsivity of a photo transistor from two light emitting diode sources of different wave lengths;

FIG. 10 is a block diagram of a circuit illustrating one embodiment of the invention;

FIG. 11 is a perspective view of a bootie using a fiber optic for transmitting at least two wave lengths of light from a remote position to the toe of the bootie;

FIG. 12, taken on line 12—12 of FIG. 11, is a lateral cross-sectional view illustrating the toe-cap of the bootie and the fiber optic for transmitting light from remotely positioned light emitting diodes and a fiber optic picking up the light after it has passed through the toe of the infant;

FIG. 13 is a block diagram of the electric circuitry for use with the bootie illustrated in FIG. 11;

FIG. 14 is a plot of the percent of light versus certain wave lengths of the light for several light emitting diodes or injection laser diodes;

FIG. 15 is a plot of the percent of light versus different wave lengths of light and illustrates a spectral distribution of electroluminescence sources;

FIG. 16 is a schematic illustration of a transmission mode analysis for analyzing components of a solution;

FIG. 17 is a schematic illustration of a reflectance mode analysis for analyzing the components of a solution;

FIG. 18 is a schematic illustration of another species of the invention, a chroma-nephelometer, primarily utilizing the reflectance mode of analysis, and secondarily the transmission mode of analysis, to analyze a suspension;

FIG. 19 is a schematic illustration of an apparatus for measuring and treating an effluent to reach a desired standard for the effluent;

FIG. 20 is a schematic illustration of an apparatus using the transmission mode of analysis for controlling the bleaching of the pulp and fiber in paper;

FIG. 21 is a schematic illustration of an apparatus for controlling, by the transmission mode of analysis, the mixing of dyes;

FIG. 22 is a schematic illustration of a dye mix process control using the transmission mode of analysis but also using a diluting agent for the dyes to achieve the proper color;

FIG. 23 is a schematic illustration of a dye mix control using the reflectance mode of analysis for controlling mixing of dye to achieve a desired color; and, FIG. 24 is a schematic illustration of a gas chromaphotometer using the transmission mode of analysis for comparing an unkown gas or a test gas with a standard gas.

THE SPECIFIC DESCRIPTION OF THE INVENTION

It is well known that infant death can result from the deprevation of oxygen in the blood stream which causes the blood to change from a state which is predominantly red to a state which will have a component of blue so that optical examination of healthy flesh will show a decidely pink tone while cyanotic flesh will be a palid gray. If an infant is diagnosed as a high-risk infant, pediatric respiratory monitors using impedance pnumography are generally employed but such apparatus must be used by carefully trained personnel and even then the equipment will not reflect true physiological events. Known optical devices have also been employed in the detection of flesh color.

Measurement of intensity of a single color source is a most unreliable procedure for the detection of color change in that it will not indicate the direction of the color change nor the magnitude of such a change.

This invention is directed to measuring a relative color shift in light passing through the blood. The light is from at least two sources of light of different wave lengths.

This invention is directed to the change in the oxycarboxy hemoglobin in the blood. A minimum of two different wave lengths of light pass through the flesh and through the blood in the capillaries in the flesh. The intensity of the wave lengths of light, from at least two sources of different wave lengths, changes upon passing through the blood in the capillaries. The blood in the capillaries acts as a filter for the light. With an increase in the concentration of carbon dioxide in the blood the relative intensities of the light sources shift toward the blue wave length. With an increase in the carbon monoxide concentration or oxygen in the blood the relative intensities of the light sources shift towards the red light.

The part of the body selected for receiving light from different light sources must be such that the light can pass through the blood in the capillaries. There are certain parts of the body that are acceptable for this. For example, the ear lobe is acceptable. Also, a finger or a toe or any part of the body through which the light can be transmitted. Other parts of the body may be the lip, the cheek, the web between the fingers and the like. If there be a bone in front of the sources of light and bone obstructs the passage of light and the intensity of light may not be detected.

It will become evident as the description proceeds that the apparatus in accordance with the invention can be arranged to monitor ventilation of an infant by optically detecting changes in blood color utilizing any suitable portion of the body such as the fingertips, ear lobes, toes or the like. For the purposes of this invention, the infant's toe has been selected as it presents little, if any, inconvenience to the infant and will avoid any possible injury. It will also be apparent that the device in the form of a bootie or a toe-cap may carry a portion of the electronic equipment for measurement of blood color and can either be wired directly or transmitted to a coordinated control system and an associated alarm. Even in the case of direct wiring, when utilizing the toe of an infant, the wiring will not restrict the infant in any way nor would it be possible for the infant to accidently become entangled and cause injury. In another form, fiber optics may be employed to transmit light from a remote point to the infant and either a photo-electric detector or fiber optic cable may be used to detect the transmitted light. A fiber optic is a means for conveying light waves from a source to the object to be observed such as the toe of an infant.

FIGS. 1 through 6 illustrate the equipment which is attached to the infant's foot 30 for the detection of the change of intensity of the blood in the capillaries in the large toe of the infant. The device is in the form of a bootie generally denoted by the numeral 32 having a sole portion 34 with upwardly extended curved sidewalls 36 and 38. The sole 34 extends forwardly to about the balls of the foot and spaced from the toes so that the infant's toes are exposed as illustrated in FIG. 2. A vertically disposed portion 40 is joined to the sole 34 and side walls 36 and 38 and extends upwardly and partly surrounds the infant's ankle. A flap 42 having a Velcro connector 44 is secured along the upper edge of the wall 36 and overlies the arch of the foot to hold the foot bootie in place on the foot of the infant. A cooperating Velcro or other similar connector 46 is affixed to the outside of the wall 38 to secure the flap 42 in position.

There are a number of issued patents teaching of the use of different types of connectors which can be used such as connectors 46 and 44. These are U.S. Pat. Nos. 3,009,235; 3,076,244; 3,147,528; 3,130,111; 3,154,837; 3,192,589; and 3,387,345.

The light sources 48 and 50 and photo-electric detector 52 for the determination of blood color are carried by a toe-cap 54 as illustrated more clearly in FIGS. 1, 2, 5 and 6. The cap 54 is adapted to slidably receive the toe of the infant and is held in position by a tongue 56 having a connector 58 for co-operation with a corresponding connector 60 on the inside of the wall 38. The light sources 48 and 50 are positioned on one side of or the top of or the bottom of the cap 54 to project light through the infant's toe and a broad-band light detector 54 is positioned on the other side or the top or the bottom of the toe to detect the light transmitted through the toe and through the blood in the capillaries in the toe. The light source 48 and 50 and the detector 52 are connected through a cable connector 58 to semiconductor control circuits generally denoted by the numerals 61 and 62 which in turn may be connected through a cable connector 64 to associated control apparatus to be described in connection with FIG. 10. If desired, the circuitry 61 and 62 may be powered by a battery 66 connected to the circuitry 61 and 62 by a suitable cable 64. In this case, transmitting and receiving means would be embodied in the circuit elements 61 and 62 or may constitute a separate structure also affixed to the wall 40 of the bootie.

As mentioned above, the invention utilizes a pair of light sources 50 and 52 which emit respectively light waves of different wave lengths such as red and green light. The intensity of the light sources is controlled and the light sources are alternately illuminated. The detector 52 senses, independently, the intensity of the red and the green light and this information is utilized to detect the onset of a color change in the infant's blood produced as a result of underventillation. With this invention, changes as small as one percent in comparable color density may be detected.

The principal of the invention is probably best understood from FIGS. 7, 8, and 9. FIG. 7 illustrates a two source system which has been found very effective and it will be observed that two light sources are employed with the green source peaking at approximately 560nM with approximately 30nM bandwidth and a red source peaking at approximately 660nM with approximately 45nM bandwidth. It will be observed that to a wide band detector (in this restricted case, one defined as capable of detecting the presence of light between the wave lengths of 500 nM and 700 nM, or the scope of FIG. 7. Although each source is distinct from the other the wide band detector cannot distinguish between the two without alternately flashing each source and synchronizing to that alternation to identify the source being flashed. In effect, the wide band detector produces an output in proportion to any source of light power input that falls between 500 nM and 700 nM. By the exclusion of ambient light and providing two light sources (as in FIG. 7), that are alternately activated and synchronized with the wide band detector's output it will be observed that the wide band detector's output, in time, expresses the relative amount of specific wave length light emission.

As in FIG. 7 it will be observed that each source, when flashed, produces approximately the same output at the detector as when the other source is flashed. This will not be the case, however, if the characteristics of the medium's color density (its ability to transmit light of specific wave lengths) changes. The medium is the physical substance that lies between the sources and the detector. In FIG. 7 it has been assumed that the medium passed equally all light of wave lengths 500 nM to 700 nM. In FIG. 7, the leftmost dotted line (which extends, though not shown, across the top of the chart to 700 nM) represents a slight shift of the medium such that if a blue source were activated and it had a peak to the left of this dotted line, then it would be greatly attenuated by the medium and the wide band detector would detect little or no emission even though the source is within the detector's scope of detection. The dotted line at the right of the graph represents the idealized characteristics of a reddish medium. With such a medium between the sources and the detector the system will interpret a high red (660 nM source) transmission to a low green (560 nM source) transmission for equal outputs from the alternately activated and synchronized sources. Thus a change from a clear (500 nM to 700 nM) medium to a reddish (about 600 nM to 700 nM) medium results in a large relative difference in the output of the detector. The system can thus distinguish a clear medium from a reddish medium. To go further, if that reddish medium's color density were to shift to allow greater transmission of shorter wave lengths (i.e., if the medium shifted from reddish to bluish or cyan as shown by the middle dotted line in FIG. 7) then correspondingly greater amounts of the light emitted from the green (560 nM) source will be detected and the relative difference between the two sources (as observed by the wide band detector through the shifting medium) will decrease. The system can thus distinguish a red medium from a cyan medium and a shift in a medium between these source defined points.

FIG. 7 illustrates an ideal case utilizing two wave lengths of light for detection of a color shift or a wave length shift. It is evident from the foregoing discussion that three or more different color light sources may also be used. A simulated practical case is illustrated in FIG. 8 which has light wave length peaks at 500, 600 and 660 nM with the peak intensity of 600 nM being substantially less than the peaks on each side thereof. The transmission of the medium C is also irregular as illustrated by the hypothetical curve C. Notwithstanding the irregularity of the transmission curve C or the irregularity of the various peak intensities, the system can be standardized by either adjusting the intensities of the sources or the sensitivity of the detector so that under normal conditions the medium will pass substantially equal intensities of the three light frequencies as interpreted by the photodetector. If the transmission of the medium C shifts to increase the transmission of red light, it is then evident that the intensity of red will increase while the intensity of the green will remain the same. Thus, a clear indication will be received that the medium is now passing increased red light. On the other hand, should the medium C change in characteristics so that it will pass less red light, then the decrease in red intensity and possibly a slight decrease in green intensity will clearly indicate the direction of shift in the color transmission characteristics of the medium toward the green or possibly the blue end of the spectrum.

FIG. 9 illustrates two color sources of light D and E and the general color (wave length) range F of the detector. While the detector may not be linear, the circuitry is arranged to compensate for the non-linearity of the detector as well as possible variations in intensity of the light sources D and E. When considering a specific case such as blood color, the sources and the detector can be coordinated to provide for example substantially uniform readings of intensity of both red and green light. Now should the blood color change by reason of cyanosis, transmission of red light will be decreased while the transmission of green light will remain the same. This is a clear indication of the change in the color transmission characteristics of the medium toward green. When this apparatus is utilized to detect blood color, a minute change in the intensity of red light as compared to the green light will provide immediate indication of the onset of cyanosis.

FIG. 10 illustrates a block diagram showing one embodiment of apparatus for the detection of blood color. In this figure, the light emitting structure 70 includes a red light source 48 and a green light source 50 which project light through the medium M such as a toe, finger, ear lobe or the like of an infant. The numeral 72 denotes a light detecting structure having a light detecting element 52. The light sources 48 and 50 are powered by drivers 74 which supply voltages alternately to the light emitters 48 and 50 and apply the same voltages to a multi-channel buffer 76 forming part of an analog to digital covertor 78. The drivers 74 are controlled by driver control circuitry 80 which in turn is controlled by the microprocessing control system 82. 80 and 82 are connected by the cable 84. The successive light pulses detected by the detector 72 indicate the intensity of the alternate red and green light pulses and are fed to a buffer amplifier 86 which functions to feed signals corresponding to red and green intensities to a multi channel buffer 88 which forms part of the analog to digital convertor 78. The signals from multi channel buffers 76 and 88 are then fed to a microprocessor controlled analog to digital convertor 90 which are then fed to the microprocessor 82. The buffers 76, and 88 also function to convert other analog monitoring information to digital information for processing by the microprocessor 82. (Such other analog information includes power supply monitoring, system performance checks, and "fail safe" indications.)

The microprocessor 82 is enabled by a keyboard 92 which among its other functions is used for instructing the microprocessor 82 to predetermined light intensity levels for the light sources 48 and 50. This is acknowledged through the cable 84, the intensity control 80 and the drivers 74. The actual voltage levels fed to the light sources 48 and 50 are monitored by means of microprocessor 82 and should the intensities deviate from a predetermined level, the microprocessor 82 will automatically make the appropriate corrections. At the same time, the microprocessor 82 is also provided with information as to the desired intensity for the received signals and this information is obtained from the buffers 76 and 88 which is then fed through the cable 94 to the microprocessor 82. The microprocessor 82 also functions to compare the relative intensities of the red and green light emission and is programmed to actuate a display 96 and/or an alarm 98 in the event there is a shift of the color transmission characteristic of the medium toward the blue end of the spectrum. With this arrangement, an exceedingly high degree of resolution is obtained with excellent stability. Deviations from normal hemogolbin content of the blood of the order of 1% of comparable color density will be detected and the alarm 98 sounded.

While the circuit elements shown in FIG. 10 can be arranged in any desired manner, normally, the circuitry denoted by the numeral 60 in FIG. 1 might include the light controls 74 and 80 and the buffer amplifier 86 while the electronic circuitry of FIG. 1 might include the analog to digital convertor 90 which includes the buffers 76 and 88 and the multi channel analog to digital convertor 90. In certain applications, it may be desirable to avoid the utilization of cables 84 and 94 connecting the bootie to the remote equipment including the microprocessor 82, programming panel 92, display 96 and alarm 98. For this purpose, a receiver 100 and a transmitter 102 would be carried by the bottie 32 and a transmitter 104 and a receiver 106 would be coupled to the microprocessor 82. In this way control information to the intensity control 80 would be handled by the transmitter 104 and receiver 100 while the sampling information from the analog to digital convertor 78 would be fed from the transmitter 102 to the receiver 106 and then to the microprocessor 82.

A modified embodiment of the invention is illustrated in FIGS. 11, 12 and 13 and like numerals have been utilized to denote corresponding components.

The bootie denoted in FIGS. 11, 12 and 13 by the reference numeral 32 is identical in basic structure to the bootie 32 of FIG. 1 except for the modified toe-cap 54 wherein the light sources 48 and 50 and the photodetector 52 are replaced by a fiber optic cable generally denoted by the reference numeral 108. The cable is formed of two main cables, namely 110 which is in fact a dual cable having optical fibers carrying, in this form of the invention, red light and green light while the portion 112 functions as the light sensor. The section 112 terminates on one side of the capillary of the toe-cap 54 while the light conducting cable 110 terminates on the other side of the capillary of the toe-cap 54 and has two discrete emitters, 48' and 50' corresponding to the light emitters 48 and 50 of FIG. 1. The reader is to understand that there may be more than two sources of light. In FIGS. 11-13 there is illustrated a cable 108 having two fiber optic cables which transmit red light and green light. However, in certain instances it may be desirable to have three or more sources of light and a corresponding number of fiber optic cables. The available colors can extend over a wide range of wave lengths. An example is the available colors may extend from the blue through the infrared. This includes blue wave lengths, green wave lengths, yellow wave lengths, orange wave lengths and red wave lengths to name a few of the wave lengths. Again, in certain applications it may be desirable to have colors from more than two light sources. The change in intensity of the colors from more than two light sources may be beneficial in determining the change in the hemoglobin and the oxy-and-carboxy hemoglobin. From a detection standpoint of this change in the oxy-and-carboxy hemoglobin a more sensitive test may be evolved. The light source can be selected from many commercially available sources such as electroluminescence sources and laser light emitting diodes (I.L.D.).

The cable 108 from the bootie 32 is a relatively flexible structure and the cable portion 110 is optically coupled with the light emitter 48' and 50' as shown in FIG. 13 while the cable portion 112 is coupled to the photoconductors 52. The electronic circuitry comprising the elements enclosed within the dashed blocks 78, 114, 116 and 118 are all disposed at a remote location from the baby and function in the same manner as previously described in connection with FIG. 10. This arrangement wherein the actual light sources 48' and 50' are disposed at a remote location affords greater latitude in obtaining the desired light intensities for detection of the onset of cyanosis and at the same time even though the equipment functions at a very low voltage; the baby is completely isolated from all electronic apparatus. In other words, there is no possibility that the baby will be electronically shocked. The fiber optics conduct the light of desired wave lengths to the baby. The light of desired wave lengths is transmitted through the capillaries of the baby. Then a shift in the detected relative amplitude of each source of the light which has been transmitted through the capillaries can be detected. If the shift in relative intensities is sufficiently large then the audible alarm 98 is activated so as to startle the baby. With the startling of the baby the baby gasps for air or breath and the concentration of carbon dioxide in the bloodstream decreases. The alarm 98 is also used to alert observers of the baby. It is to be realized that the alarm 98, although depicted as an audible alarm, can be another type of alarm such as a flashing light.

In order to provide reliable results with the invention for extended periods of time it is desirable that the light emitting and light detecting means be stable as to color and light sensitivity. Any suitable light sources and light detectors may be employed although it has been found that stable light emissive diodes can be selected to have the desired red and green response. In addition, the photodetector may take any suitable form such as a light sensitive diode or phototransitor. It is also to be understood that more than two light sources of varying colors may be employed although it has been found that in the detection of apnea, red light and green light sources have not only been found to be satisfactory but will afford more than sufficient resolution to detect a change of as little as one percent comparable color density in the color composition of the blood flowing into the capillary of the baby resulting from deprivation of oxygen and also an increased concentration of carbon dioxide in the blood. There can be used light emitting diodes, laser light emitting diodes and phototransitors. The desired light is substantially monochromatic.

The light emitting structure 70 connects with the drivers 74 by means of cables 117. The light detecting structure 72 connects with buffer amplifier 86 by means of cable 119. The reference numeral 120 will be used for all circuit components other than 48, 50, 52, 70, 72, 117 and 119. Or, in other words, the reference numeral 120 will be used for the components 74, 76, 80, 82, 86, 88, 90, 92, 94, 96, 98, 100, 102, 104 and 106 in an operative relationship. The above identified components are commercially available. In the following discussion and drawings the reference numeral 120 in association with other species of the invention will be used instead of the reference numerals for the individual components.

In FIG. 14 there is a plot of percent of light waves of certain wave lengths. FIG. 14 shows the state of the art in light emitting diode technology. FIG. 14 shows a sampling of monochromatic light over the visible range. It is to be understood that there are many more infrared devices which are availble outside of the visible range and may extend to 8,500 nM or 85,000 angstroms. Further, laser light emitting diodes, solid state lasers, also exhibit the desired monochromatic characteristics illustrated in the curves of FIG. 14. These laser light emitting diodes are suitable, if not superior, replacements for many applications. These laser light emitting diodes are also known as I.L.D.s or injection laser diodes.

In FIG. 15 there is a plot of percent of waver length for different wave lengths. FIG. 15 shows a spectral distribution of electroluminescence sources. The wave lengths from these electroluminescence sources are not monochromatic but cover a broader range than other solid state light emitters such as light emitting diodes and injection laser diodes. The electroluminescence sources are a cold light and cover some of the gaps in the present technology of cold light. The fact that these electroluminescent emitters cover a broad range of wave lengths does not diminish their useful application. One of the valuable features of these electroluminescence emitters is that under the control of applied voltage the emitters may be made to change the wave length of the light emitted so that there are different wave lengths for different applied voltages.

In FIG. 16 there is illustrated a transmission mode apparatus for analyzing the components of a solution 122. There is a tube 124 through which the solution 122 flows. It is seen that on one side of the tube 124 there is a window 126 and on the other side there is a window 128.

Associated with the window 126 are three emitters 48, 50 and 100, of light. It is to be understood that the three emitters of light emit three different wave lengths of light or three different frequencies of light. Further, it is to be understood that instead of three emitters there may be two emitters. And, it is to be understood that there may be a dozen emitters. From experience we have found that it is best to have a least two different sources of light or two different wave lengths of light.

There is associated with the window 128 the detector 72 which detects the change in wave lengths of light or the change in the frequency of the light.

The detector 72 can be responsive to a specific wave length of light or responsive to monochromatic light of a specific wave length or can be responsive to a broad spectrum of wave lengths.

In the transmission of light through the solution 122 some of the light will be absorbed by the solution and some of the light will be transmitted from the sources 48, 50 and 130 to the detectors 72. Further, it is to be understood that instead of a solution there may be a suspension of particles in the liquid. The particles may be solid, another liquid or a gas. A fundamental consideration of the apparatus of FIG. 16 is that light can be transmitted from the emitters to the detector. If light cannot be transmitted from the emitters to the detector then the reflectance system must be used instead of a transmission system.

The light emitting structure 70 connects with 120 by cable 116. The light detecting structure 72 connects with 120 by means of cable 118.

In FIG. 17 there is illustrated a tube 132 having therein a suspension 134. The suspension 134 is a fluid with particles. The fluid may be a liquid or a gas. The particles may be a solid or a liquid or a gas. In the suspension 134 the carrying vehicle is the fluid and the particles are the material being carried.

In the tube 132 there is a window 136. A minimum of two fiber optics 138 and 140 connect the window 136 with the light emitting structure 70.

A fiber optic 142 connects a window 88 with a light detecting structure 72.

The light emitting structure 70 connects with 120 by means of cables 116. The light detecting structure 72 connects with 120 by means of cable 118.

The reader is to understand that there may be more than two sources of light waves of distinct and different wave lengths and a corresponding number of fiber optics connecting with 70 and the window 136. The light wave of a certain wave length directed into the solution 134 and reflected to the fiber optic 142. With two sources of light waves the sources would be alternatively activated or pulsed.

In FIG. 18 there is illustrated another reflectance mode apparatus, a chroma-nephelometer. There is a container 144 having a window 146 in one side of the container and a window 148 in the other side of the container. In the bottom of the container there is a window 150.

There is associated with the bottom window 150 a prime illumination or a prime source of illumination, the light emitting structure 70. There is associated with the side window 148 a secondary illumination source 152. There is associated with the window 146 the light detecting element 52.

52 and 72 connect with 120 by cable 118. 48, 50 and 70 connect with 120 by cable 116. 152 connects with 120 by means of cable 154 and cable 116.

In the container 144 there is a suspension 156 comprising particles in a fluid. The fluid may be a liquid or a gas. The particles may be a solid or a liquid or a gas.

Nephelometry relates to a measurement of the amount of particles or particulants in suspension, i.e., a liquid or a gas.

In order to realize a measurement of the concentration of particles or particulants in suspension there is required side lighting, see window 148 and a secondary illumination source 152, so that the maximum particle reflection (amounting to 2% of the applied light power,) to the detector 52 through window 146 is equivalent to 100 nephlos. As such, the particles are too optically dense to pass light but will reflect the light through the window 146 to the detector 52 when the illumination is from the prime illumination source 48 and 50 at the bottom of the container 144.

The side source of illumination or the secondary illumination source 152 through window 148 is used to cancel the filtering effect of the fluid's color, viz., carrier's color, by providing a direct color test of the carrier. The particles do not affect this test from the secondary illumination source 152 through window 148 because of the high optical density of the particles. An application of chroma-nephelometer in FIG. 18 is a photo-silver reclamation, titanium alloy manufacture, the beverage industry, wastewater control, cholesterol analysis and enzyme analysis.

In FIG. 19 there is illustrated a system for measuring and treating an effluent. In many instances an effluent from a manufacturing plant must be chemically treated prior to discharge into the sewer system or must be chemically treated prior to discharging into a general area such as a body of water like a river, an ocean, a lake or a sound. In FIG. 19 there is illustrated the apparatus 160 comprising a main conduit 162 which receives the water effluent from a manufacturing plant or other unit. There is an elbow 164 connecting with the main conduit 162. In the elbow 164 there is a computer controlled valve 116. In the main conduit 162 and downstream from the connection at the elbow 164 there is a static mixer of 168.

A sampler tube 170 connects with the main conduit 162. In the sampler tube 170 there is a computer controlled valve 172. A tee 174 connects with the sampler tube 170 downstream from the valve 172 and also connects with a tube 176. In the tube 176 there is a computer controlled valve 178. The tee 174 connects with the tube 176 downstream from the valve 178.

The tee 174 connects with a mixing tube 180. In the mixing tube 180 there is a static mixer 182.

The liquid flowing through the mixing tube 180, and downstream from the static mixture 182, is subjected to light of various wave lengths. In the tube 180 there is a window 184 and a window 186. The light emitting structure 70 is adjacent to the window 184 and the light detecting element 52 is adjacent to the window 186. The structure 70 contains two separate sources of light of different wave lengths. Preferably, the source 70 should contain over two sources of different wave lengths.

A water effluent 188 containing impurities flows into the main conduit 162.

Chemicals identified as water chemistry 190 flow to the elbow 164 and through the computer controlled valve 166.

Standard test chemistry or standard test chemicals 192 flow into the tube 176 and through the computer controlled valve 178 to the mixing tube 180. In the main conduit 162 the water effluent 188 and the water treatment chemistry 190 are mixed by the static mixer 168 to form a resultant mixture 194. Then, a small part of the resultant liquid 194 is taken from the main conduit 162, downstream from the static mixer 168, and flows through the sampler tube 170 and also through the control valve 172. The test standard chemistry 192 and a sample of the resultant liquid 194 are mixed in the mixing tube 180 by means of the static mixer 182 to form a test liquid 196. Then, the test liquid flows between the light emitting structure 70 and the light detecting structure 52. The electronics associated is referred to by reference numeral 120, which has, previously been described. 70 connects with 120 by cable 116. 72 connects with 120 by cable 118.

A cable 198 connects with 120 and with the computer controlled valve 166 in the elbow 164.

An electrical line 200 connects with the computer 120 and the computer controlled valve 172 in the sampler tube 170.

An electrical line 202 connects with the computer 120 and the computer controlled valve 178 in the tube 176.

The water effluent 188 from a source such as a manufacturing facility is treated with the chemicals 190 to try and change the water effluent 188 so that it can be satisfactorily discharged into another body of water. The water effluent 188, after being treated with the appropriate chemicals 190, is discharged as resultant mixture 194.

Some of the mixture 194 is sampled and flows through the valve 172 where it is combined in the mixing tube 180 with the standard chemical or chemicals 192 to form a test liquid 196. Test liquid 196 flows between the light emitting structure 70 and the detector 52. If there is a deviation from the standard detected relative intensities in the various sources of light then the computer 120 controls the valve 166 to change the ratio of chemicals 190 to the volume of water effluent 188 so as to produce a satisfactory resultant mixture 192 which can comply with the local laws for discharge of water.

The shift in detected relative intensities of the various light waves is a result of the reaction between the components in the resultant mixture 194 and the chemicals 192. If the color shift is within a certain range then the computer controlled valve 166 will be left as is. However, if the color shift of the chemicals is greater than the normal range, then the computer controlled valve 166 will be varied so as to let an appropriate amount of chemicals 190 contact the water effluent 188 to produce a satisfactory resultant mixture 194.

The valves 172 and 178 are metering valves for metering the amount of material passing through them and to the mixing tube 180. The valves 172 and 178 provide information to the computer 120 as to the volume of liquids passing through the valves and are also controlled by the computer. The volume of liquids passing through the valves 172 and 178 are small volumes of liquid. These volumes are sufficient for test purposes and control purposes but the volume of liquids compared to the volume of resultant mixture 194 discharged is insignificant or minimal.

As part of the computer 120 there is the visual display 96 for an operator to observe.

The test liquid 196 can be discharged after passing 70 and 72.

The apparatus 160 of FIG. 19 can be used for controlling the water effluent and treating the water effluent from a manufacturing plant to make it satisfactory for discharge. Also, the apparatus 160 can be used for beverage process control to make sure that the beverage has the right concentration of chemicals.

In FIG. 20 there is illustrated an apparatus 200 for controlling the bleaching of word pulp and fibers used in paper. There is a container 202 for pulp. There is an inlet tube 204. In the tube 204 there is a control valve 206. The tube 204, downstream from the valve 206, connects with a tee 208. The aqueous effluent comprising fibers from the container 202 flows to the tee 208.

An exit tube 210 connects with the tee 208. In the exit tube 210 there is a static mixture 212.

In the exit tube 210 there is placed a source 70 of lights of various and different wave lengths and a detector 52. The exit tube 210 connects with a reaction tank 214. The reaction tank 214 contains about 85% water and about 15% pulp. The reader is to understand that the reaction tank 214 contains several thousand gallons of a mixture of pulp and water. Also, there may be a number of reaction tanks 214.

At the bottom of the reaction tank 214 there is a discharge tube 216. In tube 216 there is a source 70' of lights of various and different wave lengths and a detector 52'.

In the discharge tube 216, downstream from the source 70' and the detector 52', there is a control valve 218. The discharge tube 216 connects with the four-way cross 220 or a four-way tube 220.

There is a tube 222 which connects with the four-way tube 220. In the tube 222 there is a control valve 224.

There is a tube 226 which connects with the four-way cross 220 and leads downwardly from 220. in the tube 226 there is a static mixer 228. In the tube 226 there is a source 70" of lights of various and different wave lengths and a detector 52". The tube 226 connects with a reaction tank 230. The lower end of the reaction tank 230 connects with a tube 232. In the tube 232 there is a source 70'" of light of various and different wave lengths and a detector 52'". The tube 232 connects with a tee 240. There is a recycling tube 242 which leads from the top 240 to the four-way cross 220. In the recycling tube 242 there is a control valve 244. The pulp from the reaction tank 230, if it is not sufficiently bleached or is not bleached to desired standards, will flow through the control valve 244 and the recycling tube 242 to the four-way cross 220 and back into the reaction tank 230 for further bleaching action.

The tee 240 also connects with a discharge tube 246. In the discharge tube 246 there is a control valve 248.

A source of pulp 250 connects with the container 202 and feeds pulp 250 to the container 202.

A bleaching agent 252 connects with the inlet tube 204.

An excess bleach eliminator and wash agent 254 connects with the tube 222.

The sources of light 70, 70, and 70 contain a minimum of two different and distinct wave lengths of light. Preferably, there are more than two separate wave lengths of light. However, there are a minimum of two separate wave lengths of light. The pulp 250 flows through the exit tube 210 along with the bleaching agent 252. The pulp 250 and the bleaching agent 252 are mixed in the static mixer 212 and flow past the source of light 70 and the detector 52.

The sources of light 70, 70', 70" and 70'" and the detectors 52, 52', 53" and 54'" connect with the computer 120.

If the mixture of pulp 250 and bleaching agent 252 flowing past the source of light 70 and the detector 52 is satisfactory, the computer does not change the control valve 206. However, if there is not sufficient bleach in the mixture of pulp and bleaching agent then the valve 206 is opened to allow more bleaching agent to mix with the pulp 250. Conversely, if there is too much bleaching agent in the mixture of pulp 250 and bleaching agent 252 the valve 206 is closed somewhat to adjust the amount of bleach.

If the mixture of pulp and water and bleaching agent in the reaction tank 214 is satisfactory, then the valve 218 is allowed to remain as is. However, if there is too great a shift in the detected relative intensities of light from the source of light 70" and the pulp is not sufficiently bleached, then the value 218 is closed to a degree to allow a longer bleaching time in the reaction tank 214. Conversely, if there is too much bleaching of the pulp then the valve 218 is opened so as to allow more pulp to flow through the valve 218 for a shorter reaction time in the tank 214.

The source of light 70" and the detector 52" monitor the color of the pulp entering the reaction tank 230. The source 70" and the detector 52" are a quality control. If the pulp entering the reaction tank 230 and leaving the reaction tank 230 is satisfactory, then the valve 248 is opened to allow the pulp to flow through the discharge tube 246 for further processing such as in a Fourdrinier machine. However, if the pulp leaving the tank 230 is not sufficiently washed, this is detected by the combination of the source 70'" and the detector 52'" and the valve 248 is partially or completely closed and the valve 244 is partially or completely opened so as to recycle the pulp through the tube 242 and back to the tube 226 and the reaction tank 230.

The excess bleach eliminator and wash agent 254 flows through the tube 222 and to the valve 224. The excess bleach eliminator and wash agent 254 is a neutralizing agent for the bleaching agent 252. The eliminator and wash agent 254 flows through the tube 222 and the valve 224 to the tube 226. In the tube 226 it is mixed with the pulp from the reaction tank 214 in the static mixer 228. Also, at times the pulp from the reaction tank 230 may be recycled and flows through the tube 226 and mixes with excess bleach eliminator and wash agent 254.

The reaction tank 214 is a bleaching tank.

The reaction tank 230 is mainly a washing tank for the pulp. Also, the reaction tank 230 allows the eliminator and washing agent 254 to react with the excess bleach agent so as to neutralize the aqueous solution to a pH of about 7.

The computer 120 is the same as illustrated and described in FIG. 16 except that there are five valves to control in this instance and there are four sources of light and four detectors. However, the basic structure is the same except there are a multiplicity of valves to control, i.e., a multiplicity of stages to control, and a multiplicity of sources of light and a multiplicity of detectors.

In FIG. 20 the reader is to understand that the light from the source of light is transmitted through the solution of pulp. This is a reflectance process for reflecting the various light waves from source of light to the detector of light.

There is a display 96, as part of the computer 120 for visually displaying the various readings of the sources, detectors and valves.

The source 70 is connected by line 260 to 120. The detector 52 is connected by line 262 with 120.

The source 70' connects with 120 by line 264. The detector 52' connects with 120 by line 266.

The source 70" connects with 120 by line 268. The detector 52" connects with 120 by line 270.

The source 70'" connects by line 272 with 120. The detector 52'" connects by line 274 with 120.

The valve 206 connects with 120 by line 276.
The valve 218 connects with 120 by line 278.
The valve 224 connects with 120 by line 280.
The valve 244 connects with 120 by line 282.
The valve 248 connects with 120 by line 284.

In FIG. 20 it is seen that there is apparatus for controlling the addition of bleaching agent 252 to pulp 250. Also, there is apparatus for controlling the reaction time of the mixture of bleaching agent and pulp in the reaction tank 214.

Then, there is a means to control the amount of reaction time and washing time of the excess bleach eliminator and wash agent 254 with the mixture of bleach and pulp in the reaction tank 230. Also, there is provision, if the color of the mixture from the reaction tank 230 is not within a desired range, to recycle the mmixture back to the reaction tank 230 and, even to add additional bleach eliminator and wash agent 254.

Again, the detection of the amount of bleaching agent 252 mixed with the pulp is determined by detector 52 and source 70. Then, after the bleaching agent has bleached the pulp the quality of the pulp is sensed by source 70' and detector 52'.

Further, the amount of bleach eliminator and wash agent 254 and the mixture of pulp and bleach is detected by source of light 70 and the detector 52. Also, the quality of the bleached pulp is detected by source of light 70'" and the detector 52'". In effect, there is a control for the addition of bleaching agent to the pulp and an addition of the neutralizing agent 254 to the mixture of pulp and bleaching agent and also for the amount of wash agent.

The sources of light 70, 70', 70" and 70'" comprise at least two different wave lengths and preferably more than two wave lengths of light. The shift in the wave length as detected by the detectors 50, 50', 50" and 50'" is sent to the computer 120 which make adjustments for controlling the amount of bleaching agent added to the pulp; and the reaction time of the bleaching agent and the pulp; the addition of neutralizing agent and wash agent 254 to the pulp; and the amount of reaction time between 252 and the pulp; and, if necessary, the recycling of the mixture of pulp and a neutralizing agent 254 and the addition of a neutralizing agent 254 to the pulp and the bleaching agent.

In FIG. 21 there is an apparatus 290 for use in the mixing of two dyes to form a product of the desired color and characteristics.

The apparatus 290 comprises a main tube 292. There is a branch tube 294. In the branch tube 294 there is a value 296. The branch tube 294 connects with the main tube 292 at a tee 298. Downstream from the tee 298 there is a static mixer 300.

Downstream from static mixture 300 there is a source of light 70 and a detector 52. Again, the source of light 70 comprises two separate sources of light of two distinct wave lengths. In fact, the source 70 may comprises more than two sources of light of two separate distinct wave lengths.

There is a computer 120 which is the same as illustrated and described with respect to FIG. 16.

A line 302 connects the value 296 and the computer 120.

A line 304 connects the source 70 and the computer 120.

A line 306 connects the detector 52 and the computer 120.

There is a first dye 308 which flows into the main tube 292.

There is a second dye 310 which flows, upstream from the valve 296, into the branch tube 294. The dyes 308 and 310 meet at the tee 298 and are mixed in the static mixer 300 to form a product 312. The product flows in the main tube 292 between source 70 and the detector 52. If the color shifts of the light are within the normal range or expected range the valve is maintained at its set position.

However, if there is a color imbalance due to too much dye 310 then the detector picks up the color shifts and the computer closes, partically, the valve 296 to adjust the amount of dye 310.

Conversely, if there is a color imbalance with not sufficient dye 310 then the detector notices the phase shifts. The computer then open the valve 296 so as to allow more dye 310 to flow through the branch tube 294 and to the tee 298.

In this manner the product 312 is realized with the correct concentration of the two dyes 308 and 310.

There are appropriate openings in the main tube 292 to accomodate the source 70 and the detector 52.

It is to be realized that in certain instances there may be more than two sources of dye. There may be three or more sources of dye. However, for purposes of illustration in FIG. 21 there is a first source of dye 308 and a second source of dye 310.

In FIG. 21 the product 310 flows between the source 70 and the detector 52.

In FIG. 21 the light waves from the source 70 are transmitted through the product 310 to the detector 52.

In FIG. 21 there is illustrated a dye mixing process. However, in FIG. 22 the optical density of the product 310 may be so great that there is not sufficient transmission of light waves from the source 70 to the detector 52 to operate the computer 120. Therefore, in FIG. 22 there is added a means for diluting the product 310 and then sampling the diluted product by means of transmission of the light waves. In FIG. 22 there are similar components as in FIG. 21. Therefore, the same reference numerals will be used for the same components of FIGS. 21 and 22.

The main tube 292, downstream from the mixer 300, connects wit a tee 314. The tee 314 connects with a tube 316. In the tube 316 there is a valve 318.

The tube 316 connects with a tee 320.

There is a tube 322 which connects with the tee 320. In the tube 322 there is a valve 324.

A sampling tube 326 connects with the tee 320. In the sampling tube 326 there is a static mixer 328.

The source 70 of light waves and the detector 52 of light waves in FIG. 22 is positioned in the sampling tube 326 and not in the main tube 292.

A line 330 connects the valve 318 with the computer 120.

A line 332 connects the valve 324 with the computer 120.

The diluting agent 334 connects with the tube 322. The diluting agent may be water or another appropriate chemical such as alcohol or aldehyde or the like.

The resultant of the product 312 and the diluting agent 334 is 336 and flows between the source of light 70 and the detector 52. The resultant 336 can be discharged.

The product 312 and the diluting agent 334 are in a set proportion to become the resultant 336. If there be too great a concentration of dye 310 in the resultant 336 then there will be a shift from the desired color range for the resultant 336 and the computer 120 will command the valve 296 to close somewhat so as to decrease the concentration of dye 310.

Conversely, if there is too great a concentration of dye 308 in the resultant 336 then the computer 120 will command the valve 296 to open somewhat so as to allow a greater amount of dye 310 to flow to the tee 298.

Naturally, if the concentrations of the dyes 308 and 310 and the product 312 are satisfactory the valve 296 will not be adjusted.

The reader is to understand that the volume of liquid flowing through the valve 318 and the volume of liquid flowing through the valve 324 are small volumes of liquid. There is only enough resultant 336 flowing through the tube 326 and between the source 70 and the detector 52 so as to allow the computer 120 to analyze the light in order to control the operation of the valve 296.

Again, the apparatus of FIG. 22 is designed for use when the product 312 is of such a nature that light cannot be transmitted through the product 312. Therefore, it is necessary to dilute the product 312 to a satisfactory dilution so that light from the source 70 can pass through the product 312 and to the detector 52.

The apparatus of FIG. 22 works on the transmission principle of light passing through the resultant 336.

In FIG. 23 there is illustrated an apparatus 30 for checking the color of material produced for two dyes. In FIG. 23 the reflectance mode of analysis is used and not the transmission mode of analysis.

The apparatus 340 comprises a tube 342. In the tube 342 there is a valve 344.

There is a tube 346. In the tube 346 there is a valve 348. The tubes 342 and 346 meet at a tee 350. The tee 350 connects with a tube 352. In the tube 352 there is a static mixer 354.

Downstream from the static mixer 354 there is a valve 356.

On the end of the tube 352 there is a nozzle 358.

There is a source of light waves 70 and a detector of light waves 52. The source of light waves comprises light waves of at least two distinct wave lengths and, preferably, more than two distinct waves lengths.

There is a computer 120. The computer 120 is the same as illustrated and described with respect to FIG. 16. The source 70 connects with the computer 120 by line 360.

The detector 52 connects with the computer 120 by line 362.

The computer 120 connects by line 364 with the valve 344.

The valve 348 connects with the computer 120 by means of line 366.

The valve 356 connects with the computer 120 by means of line 368.

There is an endless belt 370.

There is a source of dye 372 which connects with the tube 342.

There is a source of dye 374 which connects with the tube 346.

The resultant product of the combination of dye 372 and of dye 374 is product 376.

In FIG. 23 there is illustrated a number of substrates 378. It is seen that the substrates 378 are on the belt 370 and pass underneath the nozzle 358. The product 376 is sprayed onto the substrates 378. Then, the substrate 378 with the product 376, now color 380, passes underneath the source 70 and the detector 52. The light waves from the source 70 are beamed to the color 380 and reflected to the detector 52. If the shift in detected relative intensities of the light wave is within the expected range the valves 344 and 348 are left as is.

However, if the shift in detected relative intensities of the light waves is out of the normal range and it appears that there is too much dye 374 then the computer 120 orders the valve 348 to be partially closed so as to decrease the amount of dye 374.

Likewise, if the color 380 is such that there is a shift in the detected relative intensities of light that indicates that there is too strong a concentration of source dye 372 then the computer orders the valve 344 to partially close so as to decrease the amount of source of dye 372.

Also, when necessary, the computer 120 can order the valves 344 and 348 to open to allow more dyes 372 and 374 to flow to the tube 352.

The computer 120 can control the valve 356 so as to control the application of the product 376 onto the substrate 378.

Further, there is an enclosure 382. This enclosure 382 eliminates stray light waves from entering the enclosure and also from contacting the color 380 on the substrate 378 and being reflected to the detector 52.

The reader is to realize that the substrate 387 may be a raw material used in the manufacture of a product or it may be a sample so as to check the concentration of the product 376 which is to be applied to another material.

Again, the apparatus 340 of FIG. 23 depends upon the reflectance of light waves and not the transmission of light waves.

In FIG. 24 there are illustrated a gas chromaphotometer apparatus 390 for comparing an unknown gas with a standard gas or a comparison gas.

There is illustrated a chamber 392 having a cavity 384. At one end there is an inlet 396. At the other end there is an outlet 398. An inlet tube 400 connects with the inlet 396. An outlet tube 402 connects with the outlet 398. At one end of the chamber 392 there is an opening 404. In the opening 404 there is an aperture 406. At the other end of the chamber 392 there is an opening 408. In the opening 408 there is an aperture 410.

The chamber 392 has the comparison gas or the standard gas.

There is a chamber 412 having a cavity 414. There is an inlet 416 in the chamber 412. There is an outlet 418 in the chamber 412. There is an inlet tube 420 connecting with the inlet 416. There is an outlet tube 422 connecting with the outlet 418. At one end of the chamber 412 there is an opening 424. There is an aperture 426 in the opening 424. At the other end of the chamber 412 there is an opening 428. There is an aperture 430 in the opening 428.

The apparatus 406, 410, 426 and 430 are of glass or plastic. The apertures transmit light waves or the apertures may be translucent.

There is associated with the chamber 392 a source 70 of light waves. The source 70 is adjacent to the aperture 406. The source 70 by means of line 424 connects with a computer 120.

There is positioned adjacent to the aperture 410 a detector 52. The detector 52 by means of line 434 connects with the computer 120.

There is a second source of light waves 70' adjacent to the aperture 426. The source 70' by means of line 436 connects with the computer 120. The detector 52 is adjacent to the aperture 430.

The detector 52 is used in connection with the two sources 70 and 70'.

There is a display 96 as part of the computer 120. Each source of light waves 70 and 70' comprise at least two different wave lengths of light. The comparison gas in the chamber 392 may be stationary or may flow through the chamber 392. The source of light waves 70 sends light waves through the chamber 392 and through the comparison gas and to the detector 52.

The unknown gas can flow through the chamber 412. The source 70' of light waves can send the light waves through the chamber 412 and to the detector 52. If there be a shift in the detected relative intensities of the light waves detector 52 will send the information to the computer 120. The computer will check the detected intensities of the light waves from the source 70' after the light waves have passed through the gas in the chamber 412 with the light waves from the source 70 after the light waves have passed through the chamber 392. If the detected relative intensities of the light waves from the chamber 412 is different than the detected relative intensities of the light waves from the chamber 392 the detector 52 senses that there are other components in the gas passing through the chamber 412 than in the gas in the chamber 342. The gas 392 in the chamber is the calibrated or the standard gas. The gas in the chamber 412 is compared with standard gas in the chamber 392.

The comparison gas in the chamber 392 may be of single gas or may be a mixture of two or more gases for standardized purposes. The gas flowing through the chamber 412 is an unknown gas and may contain components different than the components of the gas chamber 392 or may contain components in a different proportion than components of the gas in the chamber 392. By flowing the gas through the chamber 412 it is possible to have a record of the comparison of this gas with standardized gas in the chamber 392. It is possible by comparing the unknown gas with the standard gas to analyze the components in the unknown gas 412.

If the standardized gas remains the same it is not necessary to flow the gas through the chamber 392. The gas can be introduced into the chamber 392 and remain until a comparison test with the unknown gas in 412 is completed. This may be a matter of minutes or may be a matter of days. It is seen that by having an inlet and an outlet for the standard gas in the chamber 392 that it is possible to vary the composition of the standard gas so as to test different unknown gases.

The reader is to understand that the source 70 and the source 70' have at least two light sources of two different and distinct wave lengths. With a shift in the color transmission characteristics of the light as it passes through the standard gas in the chamber 392 and passes through the unknown gas in the chamber 412 it is possible to determine the composition of the components of the gas and also the proportion of the components of the gas.

Again, the source 70 and the source 70' can comprise more than two different sources of light waves. It may be desirable to have three or more sources of light waves. In our consideration we consider that the minimum number of sources of light waves should be two.

The computer 120 is the same as illustrated and described in FIG. 16. The basic structure is the same.

The gas chromaphotometer apparatus 390 is used as a quality control for the unknown gas. In the welding of metals it is necessary at times to use a gas to exclude the presence of air and to exclude the presence of oxygen. Therefore, the unknown gas or the test gas is analyzed by the apparatus 390 to determine if this gas meets the standard set for the gas used in the welding of metals. Also, in the production of gas for a fuel such as propane or such as butane the unknown gas can be passed through the chamber 412 and compared with the known standard gas in the chamber 342. Further, in the production of water gas by synthetic means it is possible to pass the water gas through the chamber 412 and compare its spectral qualities with the gas in the chamber 392 to determine if the spectral qualities fall within the normal tolerance for water gas. These are just a few of the uses of the apparatus 390 for comparing an unknown gas, in a continuous flowing unit, with a standard comparison gas.

RESUME'

This invention is directed to a method for an apparatus to determine the composition of a fluid. With the determination of the composition of the fluid it is possible to control the composition of the fluid and also to control the application of the fluid to a substrate.

There is the detection phase of the invention. Two sets of light waves of distinct and separate wave lengths are directed to the fluid. There is a first source of light waves of a known range of lengths and initial intensity. The first light waves upon leaving the fluid have a final intensity. Then, the initial intensity and the final intensity of the first source of light waves are compared. From the comparison a characteristic of the fluids is determined.

Then, light waves from a second source or a known range of wave lengths and initial intensity are directed to the fluid. The second light waves, upon leaving the fluid, have a final intensity which is determined. Then, the initial intensity and the final intensity of the second light waves are compared and a characteristic of the fluid is determined. From the comparison of both characteristics of the fluid it is possible to give partial analysis of the fluid. The reader is to understand that the light waves from the first source and the light waves from the second source are separate and distinct wave lengths. Also, the light waves from the first source and the light waves from the second source alternate so that at one time the first source of light waves are directed to the fluid and then at another time the second source of light waves are directed to the fluid.

From the characteristics of the fluid it is possible to take appropriate action. An example of this is the concentration of carbon dioxide in the blood of a baby. The light waves of the first source are directed to the flesh of a baby and then the characteristic of the blood is determined from the first source of light waves. Then, the second source of light waves is directed to the flesh of the baby and the characteristic of the blood is determined. If the light waves from the first source and the second source show a shift in the detected relative intensities and the shift indicates an increase in the concentration of carbon dioxide in the blood of the baby, then an alarm can be sounded. The alarm is to startle the baby so that the baby will inhale more fresh air to decrease the concentration of carbon dioxide in the blood. The alarm may be a bell or a buzzer or other appropriate means such as a flashing light. With an increase in the carbon dioxide in the blood of the baby the blood of the baby takes on a somewhat blue coloration. The shift in the detected relative intensities of light upon passing through the blood of the baby can indicate this increase in the blue coloration of the blood and an increase in the concentration of carbon dioxide in the blood.

The detection of the characteristic in a fluid can be by transmission of the light waves through the fluid or it can be by reflectance of the light waves from the fluid. Also, at times it may be necessary to dilute the fluid so as to have better transmission of the light waves or better reflectance of the light waves from the fluid.

From the detection of the characteristic it is possible to take appropriate action. Another example is the combining of a first fluid and a second fluid to make a product. The characteristic of the product can be determined by directing a first light wave with an initial intensity and known wave length to said product. After the first light waves have left the product determine the final intensity of the first light wave. Then, compare the known initial intensity and the final intensity to determine the characteristic of the product. Then, a second light wave of a known initial intensity and known second wave length can be directed to the product. After said second light waves have left the product determine the final intensity. Then compare the known initial intensity and the final intensity of said light waves to determine the characteristic of said product. With the characteristic of the product known it is possible to control the proportions of the first fluid and the second fluid in the product. Also, it is possible to control the quantity of the product placed on a substrate.

Another example is the controlling of the reaction time of chemicals. An example of this is in the bleaching of pulp. The pulp and the bleach agent are combined to form an active pulp mixture. By means of two light waves of distinct and separate wave lengths it is possible to detect a characteristic of the aqueous pulp mixture. From this characteristic it is possible to control the proportions of the bleach agent and the pulp. The bleach agent and the pulp make an intermediate product. With the aid of two light waves of distinct and separate wave lengths it is possible to detect a characteristic of the intermediate product. This characteristic of the intermediate product can result in controlling the reaction time of the bleach agent and the pulp. Then, the intermediate product can be mixed with a chemical such as an excess bleach eliminator and washing agent to form an aqueous chemical mixture. With the aid of two light waves of separate and distinct wave lengths it is possible to determine the characteristic of the aqueous chemical mixture. With this characteristic of the aqueous chemical mixture, it is possible to control the proportions of the excess bleach eliminator and wash agent and to intermediate product. The aqueous chemical mixture is allowed to react so that the result is a test product. With the aid of two separate and distinct light waves it is possible to detect a characteristic of a test product. From the characteristic of the test product it is possible to recycle the aqueous mixture or the test product to allow more reaction time or it is possible to discharge the test product as bleached pulp. The bleached pulp may be further processed so as to make sheets of pulp in a fourdrinier machine.

The reader is to understand that there may be more than two sources of light waves. There may be three or four or more sources of light waves wherein each light wave is of a separate and distinct wave length from the other light waves. Generally, the more sources of light waves, the more discriminatory is the test for determining the characteristic of a fluid. The number of sources of light waves will be a compromise between the cost of the detection and control apparatus and also the discrimination necessary in determining the characteristic of the fluid.

In preparation of this patent application, a patent search was made. The patents found in this patent search are:

H. Boucke, U.S. Pat. No. 2,755,796;
A. D. Kompelien et al, U.S. Pat. No. 3,040,737;
H. K. Richter, U.S. Pat. No. 3,167,658;
E. A. Fitter et al, U.S. Pat. No. 3,228,391;
R. A. Harte, U.S. Pat. No. 3,463,142;
Strom et al, U.S. Pat. No. 3,465,550;
Strom et al, U.S. Pat. No. 3,486,971;
A.T. Kissen, U.S. Pat. No. 3,572,331;
Kawai, U.S. Pat. No. 3,743,429;
Petit, U.S. Pat. No. 3,831,586;
Jacobs, U.S. Pat. No. 3,882,847;
Konishi et al, U.S. Pat. No. 3,998,550;
Kuska et al, U.S. Pat. No. 4,030,484;
Lee, U.S. Pat. No. 4,050,452;
Lawson, Jr., U.S. Pat. No. 4,146,885;
Peirce et al, U.S. Pat. No. 4,195,642;
Raemer et al, U.S. Pat. No. 4,211,239.

We consider that none of these patents anticipate our invention. They do not compare the shift in initial relative intensities of separate light sources after being directed to a fluid and then detecting the final relative intensities after it has left the fluid to determine the characteristic. Our invention is based on two or more sources of light waves of distinct and separate wave lengths. These light waves are directed to a fluid. The initial relative intensities of the light wave being directed to the fluid is known. The final relative intensities of the light waves after the light wave has left the fluid is known. The shift or the difference in the initial and final relative intensities can be compared to determine a characteristic of the fluid. Again, we consider that none of the references teach of this technique.

We consider the invention to be new and unobvious as we do not know of any teaching or any prior art teaching the use of two or more light waves which have distinct and separate wave lengths for determining the characteristic of a fluid. Since we do not know of any prior teaching we consider the invention to be new and unobvious.

Also, we consider the invention to be useful as with the determination of the characteristic of fluid it is possible to make changes or control the fluid. An example is the detection of carbon dioxide in the blood of a living organism such as a baby. With an increase of the concentration of carbon dioxide in the blood of a baby it is possible to activate and alarm to notify a party to contact the baby to try and get the baby to breath more air or else to startle the baby to breath more air. Further, the invention is useful from the standpoint of detecting the characteristic or characteristics of a fluid so that the fluid can be altered or so that the fluid can be allowed to be in residence for a longer period of time for reaction to occur.

We claim:

1. An apparatus for controlling the proportions of a first fluid and a second fluid, said apparatus comprising:
    a. a combining means for combining said first fluid and said second fluid to form a product;
    b. a substrate;
    c. a means to apply said product to said substrate to form a color on said substrate;
    d. a source of first light waves of an initial intensity;
    e. a directing means to direct said first light waves to said color on said substrate;
    f. after said first light waves have left said color determining the final intensity of said first light waves by a determining means;
    g. a means to compare said initial intensity and said final intensity of said first light waves to determine a characteristic of said color and thereby a characteristic of said product;
    h. a source of second light waves of an initial intensity;
    i. a directing means to direct said second light waves to said color on said substrate;
    j. after said light waves have left said color and said substrate a determining means to determine the final intensity of said second light waves;
    k. a means to compare said initial intensity and said final intensity of said second light waves to determine a characteristic of said color and thereby a characteristic of said product; and,
    l. a control means operatively connecting with said means to compare said initial intensity and said final intensity of said first light waves to control the proportion of said first fluid in said product and a control means operatively connecting with said means to compare said initial intensity and said final intensity of said second light waves to control the proportion of said second fluid in said product.

2. An apparatus according to claim 1 and comprising:
    m. a control means to control the quantity of said product applied to said substrate.

3. An apparatus according to claim 1 and comprising:
    m. said first light waves and said second light waves being of distinct and separate wave lengths and, of, substantially, monochromatic origin such as light emitting diode, injection laser diode, laser light emitting diode and a source of electroluminescence; and,
    n. alternately directing said first light waves to said product and said second light waves to said product so that while said first light waves are directed to said product said second light waves are not directed to said product and while said second light waves are directed to said product said first light waves are not directed to said product.

4. An apparatus according to claim 3 and comprising:
    o. said first light waves or initial intensity being first analog;
    p. a means to convert said first analog to first digital;
    q. said first light waves of final intensity being second analog;
    r. a means to convert said second analog to second digital;
    s. a microprocessor for comparing said first digital and said second digital to determine said characteristic of said color;
    t. said second light waves of initial intensity being third analog;
    u. a means to convert said third analog to third digital;
    v. said second light waves of final intensity being fourth analog;
    w. a means to convert said fourth analog to fourth digital; and,
    x. a microprocessor for comparing said third digital and said fourth digital to determine said characteristic of said color.

5. An apparatus according to claim 4 and comprising:
    y. said control means comprising a valve to control the proportion of said first fluid in said product; and,
    z. said control means comprising a valve to control the proportion of said second fluid in said product.

6. An apparatus according to claim 5 and comprising:
    aa. a control means to control the quantity of said product applied to said substrate.

7. An apparatus according to claim 6 and comprising:
    bb. a means to prevent light waves other than said first light waves and said second light waves contacting said color on said substrate.

8. An apparatus according to claim 3 and comprising:
    o. a driver operatively connecting with said source of first light waves and said source of second light waves;
    p. said determining means being a light detecting structure;
    q. said light detecting structure operatively connecting with a first buffer;
    r. said driver operatively connecting with a second buffer;
    s. said first buffer and said second buffer connecting with an analog to digital converter;
    t. said analog to digital converter operatively connecting with a microprocessor.
    u. said first light waves of initial intensity being first analog;
    v. said first light waves of final intensity being second analog;
    w. said second light waves of initial intensity being third analog; and,
    x. said second light waves of final intensity being fourth analog.

9. An apparatus according to claim 8 and comprising:
    y. said control means comprising a valve to control the proportion of said first fluid in said product; and,
    z. said control means comprising a valve to control the proportion of said second fluid in said product.

10. An apparatus according to claim 9 and comprising:
    aa. a control means to control the quantity of said product applied to said substrate.

11. An apparatus according to claim 10 and comprising:
    bb. a means to prevent light waves other than said first light waves and said second light waves contacting said color on said substrate.

12. An apparatus according to claim 8 and comprising:
    y. a driver control operatively connecting with said driver and with said microprocessor.

13. An apparatus according to claim 8 and comprising:
   y. a buffer amplifer operatively connecting with said determining means and with said first buffer.

14. An apparatus according to claim 8 and comprising:
   y. a microprocessor control operatively connecting with said microprocessor to control the source of first light waves to a predetermined initial intensity and to control the source of second light waves to a predetermined initial intensity.

15. An apparatus according to claim 8 and comprising:
   y. a driver control operatively connecting with said driver and with said microprocessor;
   z. a buffer amplifer operatively connecting with said determining means and with said first buffer; and,
   aa. a microprocessor control operatively connecting with said microprocessor to control the source of first light waves to a predetermined initial intensity and to control the source of second light waves to a predetermined initial intensity.

16. An apparatus according to claim 1 and comprising:
   m. said first light waves being reflected from said color and said determining means determining the final intensity of said first light waves; and,
   n. said second light waves being reflected from said color and said determining means determining the final intensity of said second light waves.

17. An apparatus according to claim 16 and comprising:
   o. said first light waves and said second light waves being of distinct and separate wave lengths and, of substantially monochromatic origin such as light emitting diode, injection laser diode, laser light emitting diode and a source of electroluminescence; and,
   p. alternately directing said first light waves to said product and said second light waves to said product so that while said first light waves are directed to said product said second light waves are not directed to said product and while said second light waves are directed to said product said first light waves are not directed to said product.

18. An apparatus according to claim 17 and comprising:
   r. said first light waves of initial intensity being first analog;
   s. a means to convert said first analog to first digital;
   t. said first light waves of final intensity being second analog;
   u. a means to convert said second analog to second digital;
   v. a microprocessor for comparing said first digital and said second digital to determine said characteristic of said color;
   w. said second light waves of initial intensity being third analog;
   x. a means to convert said third analog to third digital;
   y. said second light waves of final intensity being fourth analog;
   z. a means to convert said fourth analog to fourth digital; and,
   aa. a microprocessor for comparing said third digital and said fourth digital to determine said characteristic of said color.

19. An apparatus according to claim 18 and comprising:
   aa. said control means comprising a valve to control the proportion of said first fluid in said product; and,
   bb. said control means comprising a valve to control the proportion of said second fluid in said product.

20. An apparatus according to claim 19 and comprising:
   cc. a control means to control the quantity of said product applied to said substrate.

21. An apparatus according to claim 20 and comprising:
   dd. a means to prevent light waves other than said first light waves and said second light waves contacting said color on said substrate.

22. An apparatus to claim 18 and comprising:
   b. a driver control operatively connecting with said driver and with said microprocessor.

23. An apparatus according to claim 18 and comprising:
   bb. a buffer amplifier operatively connecting with said determining means and with said first buffer.

24. An apparatus according to claim 18 and comprising:
   bb. a microprocessor control operatively connecting with said microprocessor to control the source of first light waves to a predetermined initial intensity and to control the source of second light waves to a predetermined initial intensity.

25. An apparatus according to claim 18 and comprising:
   bb. a driver control operatively connecting with said driver and with said microprocessor;
   cc. a buffer amplifier operatively connecting with said determining means and with said first buffer; and,
   dd. a microprocessor control operatively connecting with said microprocessor to control the source of first light waves to a predetermined initial intensity and to control the source of second light waves to a predetermined initial intensity.

* * * * *